US008865427B2

(12) United States Patent
Poo et al.

(10) Patent No.: US 8,865,427 B2
(45) Date of Patent: Oct. 21, 2014

(54) PERIFUSION DEVICE

(75) Inventors: Ramon E. Poo, Miami, FL (US);
Camillo Ricordi, Miami, FL (US);
Felipe Echeverri, Miami, FL (US);
Over Cabrera, Deerfield Beach, FL (US); Per-Olof Berggren, Miami, FL (US)

(73) Assignees: Biorep Technologies, Inc., Miami, FL (US); University of Miami, Miami, FL (US)

(*) Notice: Subject to any disclaimer, the term of this patent is extended or adjusted under 35 U.S.C. 154(b) by 0 days.

(21) Appl. No.: 13/595,697

(22) Filed: Aug. 27, 2012

(65) Prior Publication Data

US 2013/0040324 A1 Feb. 14, 2013

Related U.S. Application Data

(60) Division of application No. 12/827,703, filed on Jun. 30, 2010, now Pat. No. 8,263,389, which is a continuation-in-part of application No. 11/653,193, filed on Jan. 12, 2007, now Pat. No. 8,785,178.

(51) Int. Cl.
| | |
|---|---|
| *C12Q 1/18* | (2006.01) |
| *C12M 3/00* | (2006.01) |
| *C12M 1/34* | (2006.01) |
| *C12M 1/00* | (2006.01) |
| *C12M 1/32* | (2006.01) |

(52) U.S. Cl.
CPC ............... *C23M 41/48* (2013.01); *C12M 23/42* (2013.01); *C12M 41/00* (2013.01); *C12M 23/40* (2013.01); *C12M 23/12* (2013.01)

USPC ..... 435/32; 435/286.5; 435/287.3; 435/293.1

(58) Field of Classification Search
CPC ........ C12Q 1/18; C12M 23/12; C12M 23/40; C12M 23/42; C12M 23/50; C12M 23/58; C12M 25/18; C12M 41/48
USPC .................... 435/286.5, 293.1, 299.1, 32, 33; 422/514, 537, 539
See application file for complete search history.

(56) References Cited

U.S. PATENT DOCUMENTS 4,650,766 A 3/1987 Harm et al.
4,959,321 A 9/1990 Preece et al.
(Continued)

OTHER PUBLICATIONS

Cabrera, et al., "Glutamate is an autocrine signal essential for glucagon release." (21 pages).

(Continued)

*Primary Examiner* — William H Beisner
(74) *Attorney, Agent, or Firm* — Novak Druce Connolly Bove + Quigg LLP

(57) ABSTRACT

A perifusion device includes at least one sample container for cells, the sample container having an inlet and an outlet. The container receives test liquid through the inlet and discharges the liquid through the outlet. A manifold having a plurality of liquid inlets, control valves, and liquid outlets can be provided. A receptacle housing has a plurality of receptacles. A drive is connected to the receptacle housing for moving the receptacle housing. A programmable controller can be provided to control movement of the receptacle housing. The test liquid includes at least one stimuli for the cells. The liquid collected in the receptacles is analyzed to determine the response of the cells to the stimuli.

21 Claims, 27 Drawing Sheets

(56) References Cited

U.S. PATENT DOCUMENTS

| | | | |
|---|---|---|---|
| 5,079,160 A | 1/1992 | Lacy et al. |
| 5,424,209 A | 6/1995 | Kearney |
| 6,416,718 B1 | 7/2002 | Maiefski et al. |
| 6,548,263 B1 | 4/2003 | Kapur et al. |
| 6,653,124 B1 | 11/2003 | Freeman |
| 6,660,149 B1 | 12/2003 | Karger et al. |
| 7,323,092 B2 | 1/2008 | Karger et al. |
| 2002/0110905 A1* | 8/2002 | Barbera-Guillem et al. ............ 435/294.1 |
| 2003/0069413 A1 | 4/2003 | Pai et al. |

OTHER PUBLICATIONS

Cabrera, et al., "Glutamate is a positive autocrine signal for glucagon release," Cell Metabolism (2008) 7: 545: 554.

\* cited by examiner

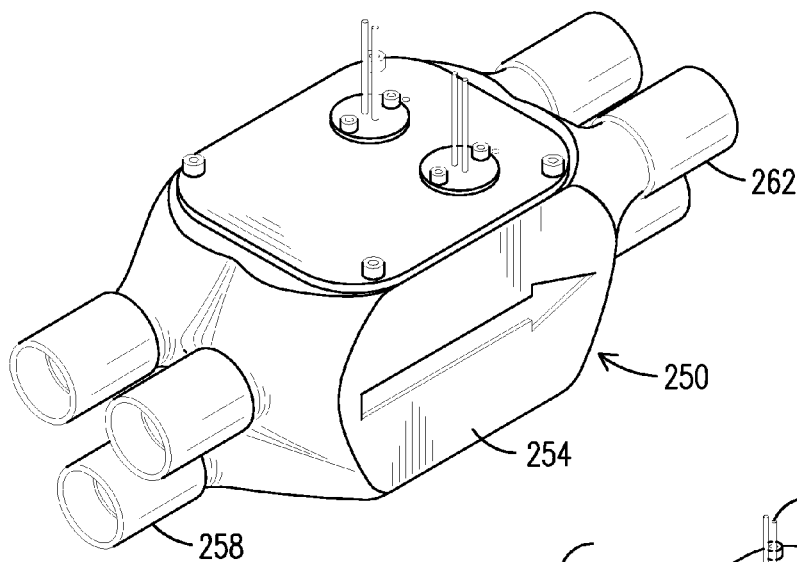
FIG. 29
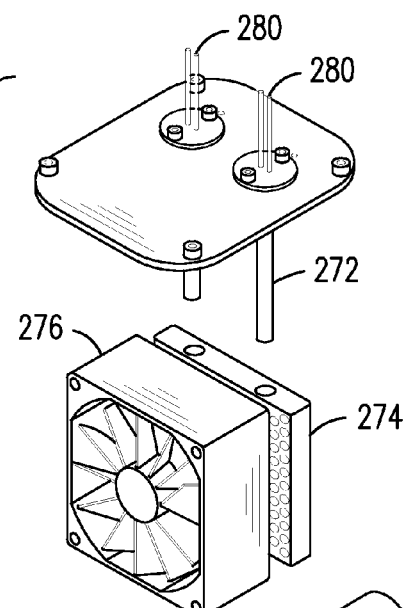
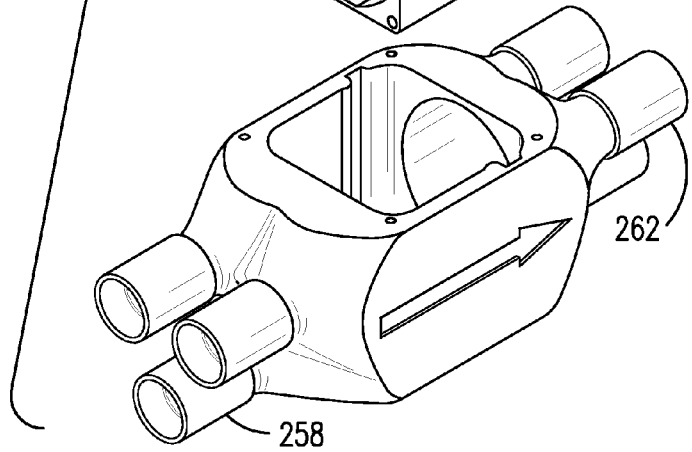
FIG. 30

PERIFUSION DEVICE

CROSS REFERENCE TO RELATED APPLICATIONS

This Application claims priority to and is a divisional of U.S. patent application Ser. No. 12/827,703, filed Jun. 30, 2010, now U.S. Pat. No. 8,263,389, which claims priority to U.S. patent application Ser. No. 11/653,193, filed Jan. 12, 2007, now U.S. Pat. No. 8,785,178, the entirety of which are incorporated herein by reference.

BACKGROUND OF THE INVENTION

The response of cells to various stimuli can provide important information about the cells. This information can be useful from a research perspective in discovering and ultimately understanding the reactions of cells to these stimuli. These responses can also have utility in testing the viability and health of the cells. For example, healthy pancreatic islet cells when stimulated with glucose will produce insulin. The rate of production of insulin can provide an indication of the viability of these cells. In order to determine the rate of production, several samples are often taken at intervals and tested for the presence of insulin.

Perifusion is the process of passing a fluid past cells or tissue immersed in the fluid. Apparatus for performing perifusion experiments are usually made from available equipment in the laboratory. The cells are placed into a packed column and inlet and outlet tubing is attached to the column. A solution including the stimuli, such as glucose, is flowed through the column and samples are periodically taken from the column through the outlet and tested for the presence of insulin. The process is time and labor intensive. An attendant must regularly draw and test the samples. In order to provide sufficient data, several samples are usually run simultaneously. In this case, output must be regularly taken from several columns and the samples analyzed for the presence of insulin or whatever products are being measured.

SUMMARY OF THE INVENTION

A perifusion device comprises a sample container. The sample container has a liquid inlet and a liquid outlet, the container receiving liquid through the inlet and discharging through the outlet. A receptacle housing has a plurality of receptacles for receiving fluid from the outlet of the sample container. A drive is connected to the receptacle housing for moving the receptacle housing such that samples from the outlet are collected in the plurality of receptacles. A liquid source can be provided for supplying test liquid to the container.

The perifusion device can further comprise a plurality of sample containers. The plurality of receptacles are positioned in the receptacle housing such that different receptacles receive samples from different liquid outlets of the sample containers. The receptacles can be arranged in rows and columns. The liquid outlets of the sample containers can then be aligned in a row, the rows of receptacles being aligned with the row of liquid outlets to receive samples from the sample containers, such that movement of the receptacle housing by the drive will cause successive receptacles in the columns to receive successive samples from the sample containers. The receptacle housing can be a tray. The tray can have a plurality of receptacles. The receptacles can be in the shape of wells or any other suitable construction.

The sample containers can be columns. The sample containers can be packed with substrate. The substrate can be any suitable substrate, such as beads or gel. The sample container can be constructed so as to permit disassembly, and a portion can be dimensioned to fit within a microcentrifuge tube.

A pump can be provided for causing the test liquid to flow through the column. The pump controls the volumetric flow rate through the sample container. The pump can be a peristaltic pump.

Control means can be provided for operating the drive to move the receptacle housing at predetermined times. The control means is preferably programmable.

At least one sensor can be provided for sensing a characteristic of the fluid. The sensor can be positioned upstream or downstream of the sample, and it is possible to provide sensors both upstream and downstream of the sample.

The cell stimulus can comprise a compound, the compound being at least one selected from the group consisting of carbohydrate, lipid, and peptide. The stimulus can also be any compound in the nature of a drug, which stimulates the behavior of the cells under study in some detectable way.

At least one analytical device can be provided for detecting at least one analyte in the liquid. At least one temperature controller for controlling the temperature of the liquid flowing through the sample container can be provided.

Means for changing the stimulus in a liquid flowing through the sample container can be provided. The means can comprise at least one valve for altering the flow of the stimulus through the sample container. A plurality of valves can be provided, where the valves direct the flow of different test liquids from different liquid sources to a manifold. The manifold directs flow to a sample container.

A method for performing perifusion according to the invention comprises the step of providing a perifusion device. The perifusion device comprises at least one sample container, the sample container having a liquid inlet and a liquid outlet. The container receives liquid through the inlet and discharges the liquid through the outlet. A receptacle housing has a plurality of receptacles for receiving fluid from the outlet of the sample container. A drive is connected to the receptacle housing for moving the receptacle housing such that samples from the outlet are collected in the receptacles.

Cells are placed into the sample container. At least one stimulus for the cells is provided in a test liquid. The test liquid containing the stimulus is caused to flow through the sample container. The liquid is collected from the outlet of the sample container in one of the receptacles. The drive is operated to move the receptacle housing, and at least one additional sample is collected in at least one additional receptacle of the receptacle housing. The response of the cells to the stimulus in the collected samples is then detected.

A method for testing the viability of cells according to the invention comprises the step of placing the cells into a sample container. At least one stimulus for the cells is provided in a test liquid. The test liquid containing the stimulus is caused to flow through the sample container, the stimulus resulting in an indication of cell health that is detectable in liquid leaving the sample container. The liquid is collected from the outlet of the sample container in the receptacles. The response of the cells to the stimulus in the collected samples is then detected and used to determine viability. The method can further comprise the step of determining the number of cells in the sample, which can be used to normalize the data. The number of cells in the sample can be determined by any suitable method, such as measuring the amount of DNA in the sample.

In another aspect of the invention, a perifusion device includes a plurality of sample containers. The sample containers have a liquid inlet and a liquid outlet. The containers receive liquid through the inlet and discharge through the liquid outlet. A receptacle housing has a plurality of receptacles for receiving liquid from the outlets of the sample containers. The plurality of receptacles is positioned in the receptacle housing such that different receptacles receive samples from different liquid outlets of the sample containers. A drive is connected to the receptacle housing for moving the receptacle housing such that samples from the liquid outlets of the sample containers are successively collected in different ones of the plurality of receptacles. A valve manifold has a plurality of liquid inlets and a plurality of liquid outlets, and a plurality of flow junctions connecting the liquid inlets to the liquid outlets. At least one valve is disposed between each liquid inlet and each flow junction. The liquid outlets of the valve manifold are connected to the liquid inlets of the sample containers. A plurality of liquid sources for supplying liquid to the liquid inlets are provided. Each liquid source is in liquid connection to one of the liquid inlets of the valve manifold. A programmable controller for controlling the operation of the valves and the flow of liquid from the liquid sources to the mixing sites, and thereby to the sample containers, is also provided.

Each of the liquid inlets is connected to a liquid inlet conduit of the manifold, the liquid inlet conduit having a plurality of branch lines, and each branch line is connected to at least one of the flow junctions and has a valve associated with the branch line to control liquid flow through the branch line and to the flow junction. Each flow junction can connect to a plurality of liquid outlets of the valve manifold. Each flow junction can connect to a plurality of the branch lines and to a plurality of liquid inlets and liquid sources.

The receptacles can be arranged in rows and columns and the liquid outlets of the sample containers can be aligned in a row. The rows of receptacles can be aligned with the row of liquid outlets to receive samples from the sample containers. Movement of the receptacle housing by the drive causes successive rows of receptacles in the columns to receive successive samples from the sample containers.

The receptacle housing can be a tray. The tray can be detachably securable to a receptacle drive assembly in either landscape or portrait positions. A heater can be provided for heating gas flowing through the perifusion device. The heater can have a plurality of gas inlets and a plurality of gas outlets.

The perifusion device in another aspect can have first and second sample containers. The output of the first sample containers flows into and becomes the input for the second sample containers.

A method for performing perifusion, includes the steps of: providing a perifusion device, the perifusion device comprising a plurality of sample containers having a liquid inlet and a liquid outlet, the containers receiving liquid through the inlet and discharging through the outlet; a receptacle housing having a plurality of receptacles for receiving liquid from the outlet of the sample container, the plurality of receptacles being positioned in the receptacle housing such that different receptacles receive samples from different liquid outlets of the sample containers; a drive connected to the receptacle housing for moving the receptacle housing such that samples from the liquid outlets of the sample containers are successively collected in different ones of the plurality of receptacles; a valve manifold having a plurality of liquid inlets and a plurality of liquid outlets, and a plurality of flow junctions connecting the liquid inlets to the liquid outlets, and at least one valve disposed between each liquid inlet and each mixing site; a plurality of liquid sources for supplying liquid to the containers, each liquid source being connected to one of the liquid inlets of the valve manifold; the liquid outlets of the valve manifold being connected to the liquid inlets of the sample containers; and, a programmable controller for controlling the operation of the valves and the flow of liquid from the liquid sources to the mixing sites, and thereby to the sample containers;

placing sample cells into the containers;

providing in the liquid sources at least one stimulus for the cells;

causing the liquid containing the stimulus to flow through the valve manifold;

operating the control means to cause the valves to control the flow of liquids from the liquid sources to the flow junctions, the liquids being mixed in the flow junctions and exiting through the liquid outlets to the inlets of the sample containers;

collecting the liquid from the liquid outlets of the sample containers in the receptacles;

causing the drive to move the receptacle housing;

collecting at least one additional sample in at least one additional receptacle; and, detecting the response of the cells to the stimulus in the collected samples.

A device for conducting perifusion can include first and second liquid source containers. The source containers have differing concentrations of a substance. A pump is connected to each source container for metering determined flow rates from each source container. A flow junction is provided for combining the flows from each source container. The output from the flow junction is directed to at least one sample container. A receptacle housing has a plurality of receptacles for receiving liquid from outlets of the sample container. The plurality of receptacles is positioned in the receptacle housing such that different receptacles sequentially receive liquid output from the outlet of the sample container. A drive is connected to the receptacle housing for moving the receptacle housing such that samples from the liquid outlet of the sample container are successively collected in different ones of the plurality of receptacles. A programmable controller is provided for controlling the operation of the pumps and the combining of the flows to obtain a desired final concentration of the substance flowing into the sample container.

BRIEF DESCRIPTION OF THE DRAWINGS

There are shown in the drawings embodiments which are presently preferred, it being understood, however, that the invention can be embodied in other forms without departing from the spirit or essential attributes thereof.

FIG. 29 is a perspective view of a heater assembly.

FIG. 30 is an exploded perspective of a heater assembly.

DETAILED DESCRIPTION OF THE INVENTION

Figure 1:
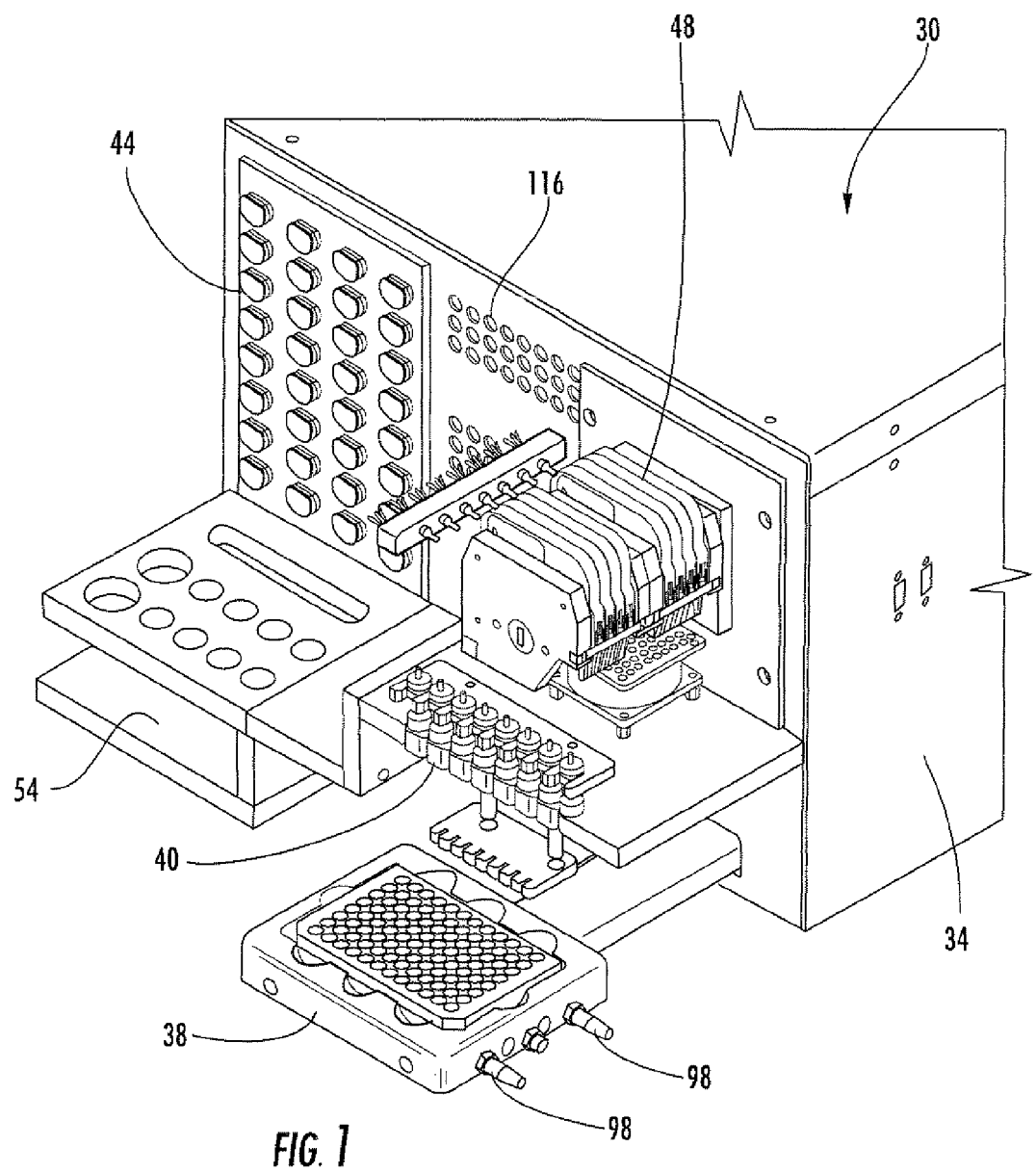
FIG. 1 is a perspective view of a perifusion device according to the invention.
Figure 2:
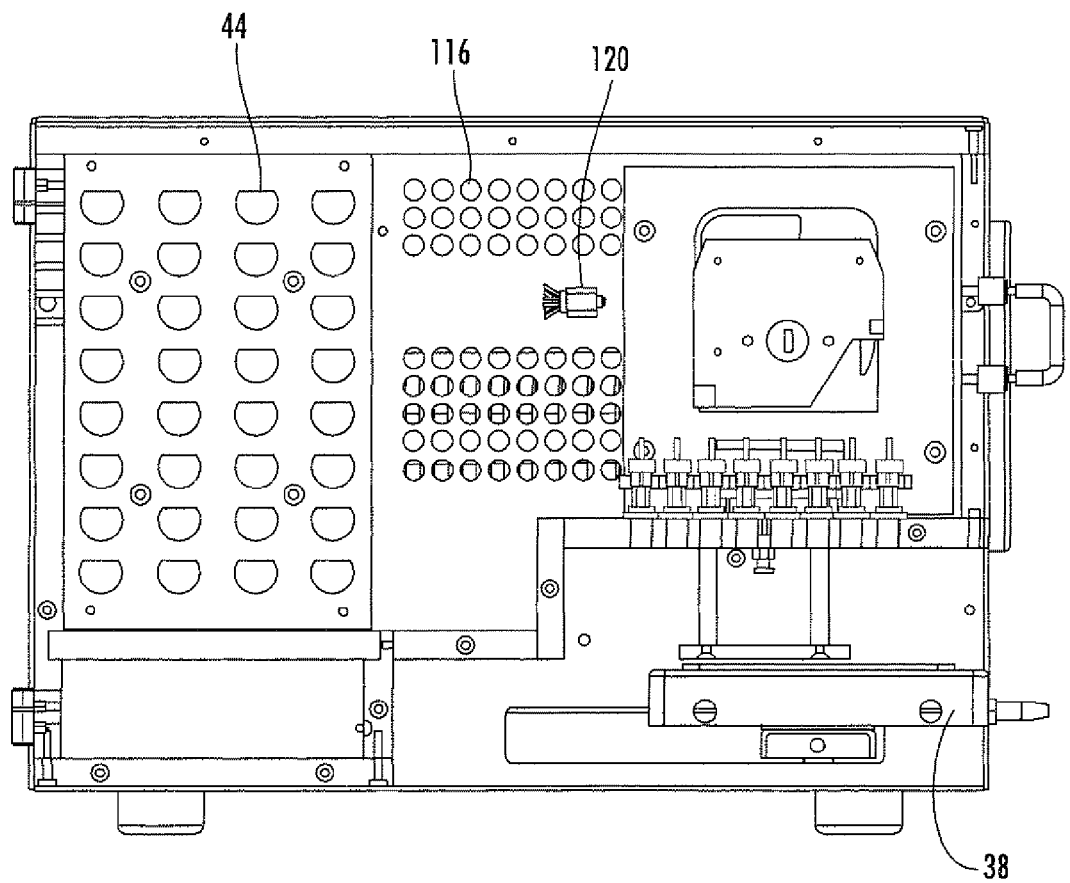
FIG. 2 is a front elevation.
Figure 3:
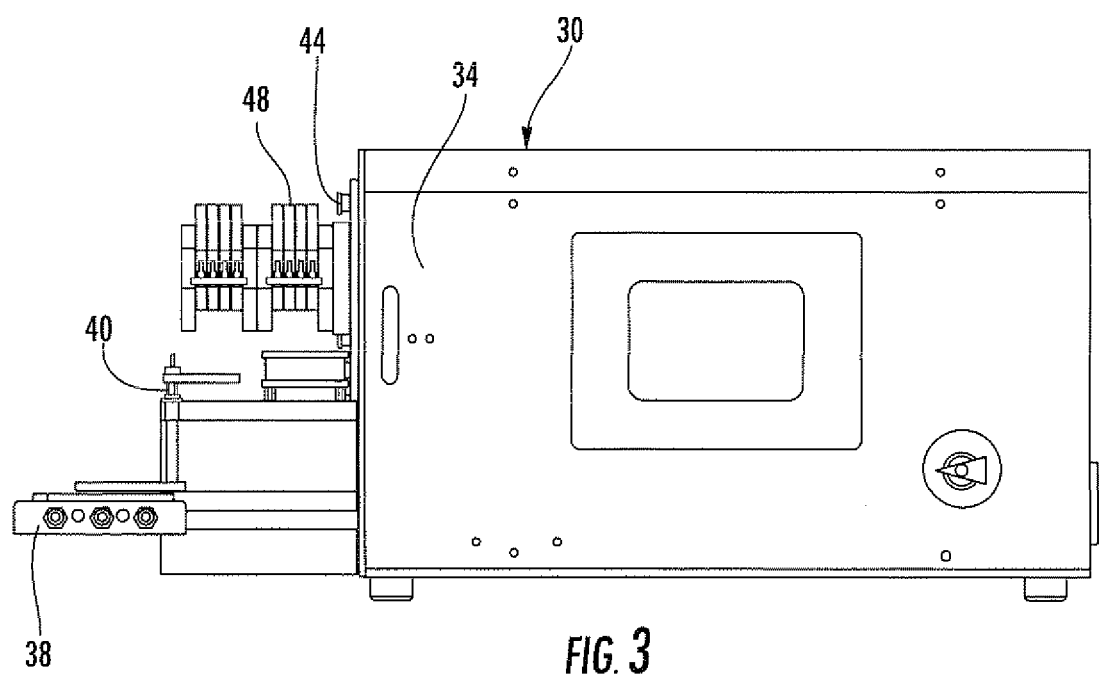
FIG. 3 is a right side elevation.
Figure 4:
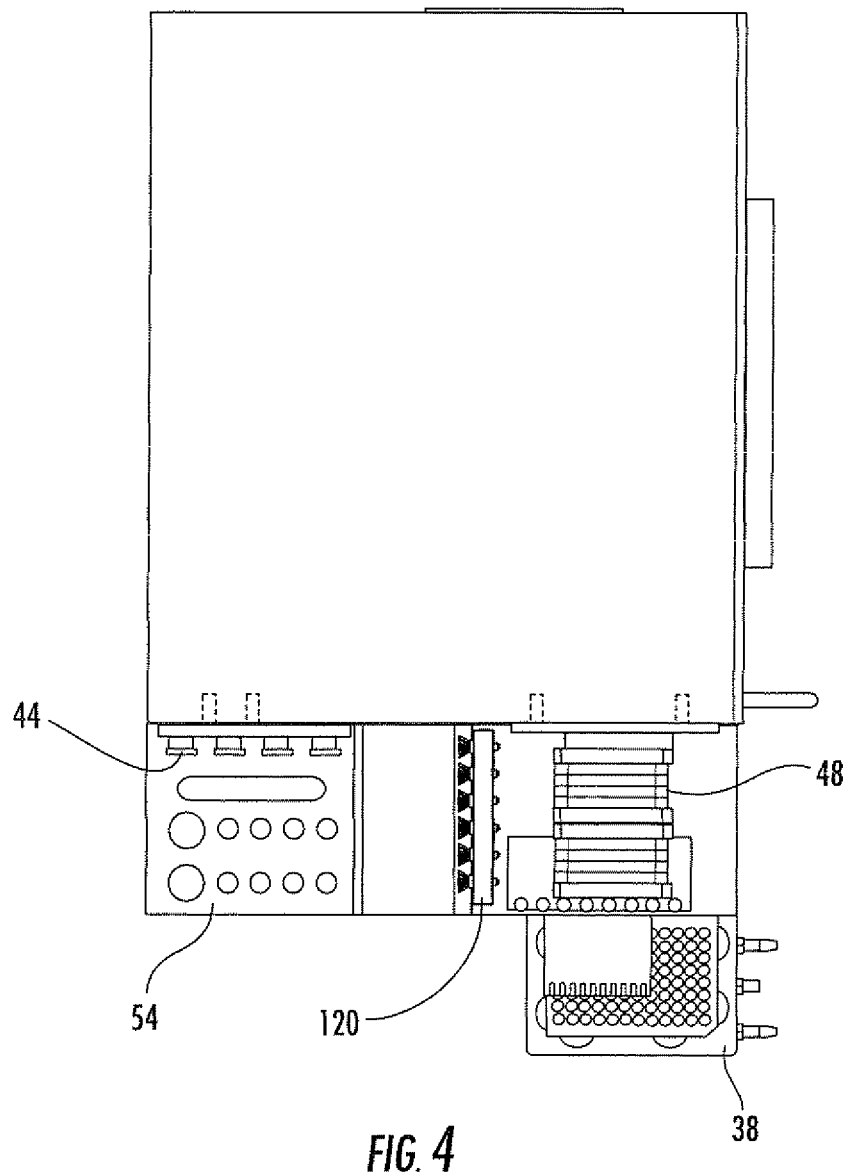
FIG. 4 is a top plan view.
Figure 5:
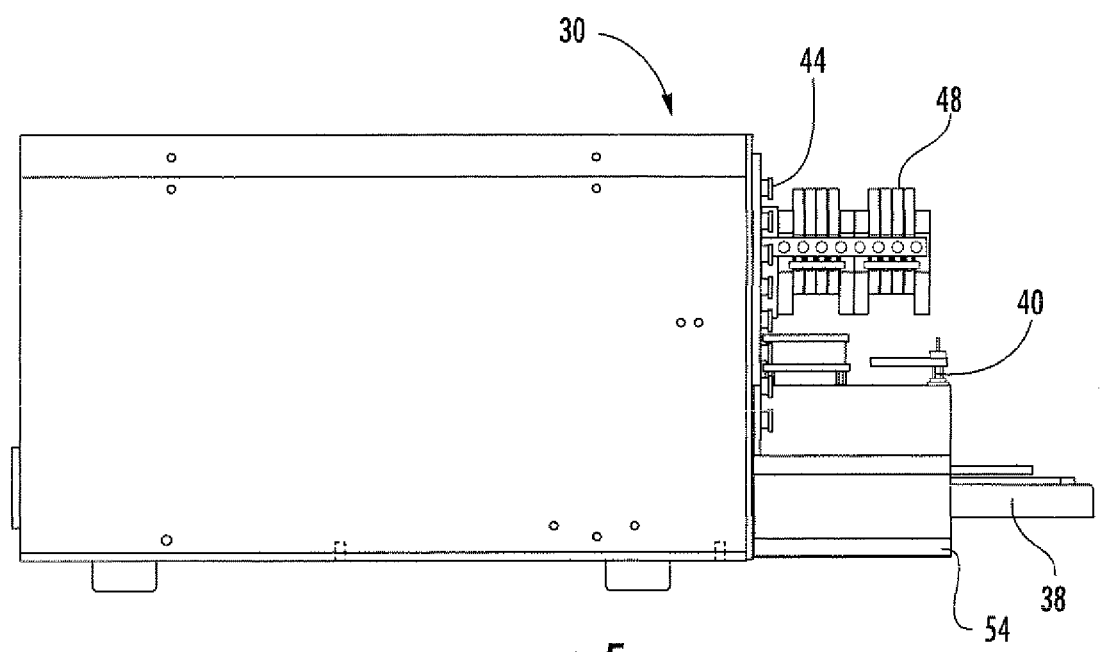
FIG. 5 is a left side elevation.

There is shown in FIG. 1 a perifusion device 30. The perifusion device 30 has a housing 34 and a receptacle housing 38. A plurality of sample containers 40 are mounted generally above the receptacle housing 38. A plurality of valves 44 are used to control the flow of test liquids and compounds from source containers to the sample containers 40. Suitable pumping apparatus such as pump assembly 48 is provided to control the flow of solution through the sample containers 40. Flow from the source containers is controlled by suitable structure such as the valves 44 and the pump 48 to direct solutions through the sample containers 40. Several different pump/valve constructions and designs can be utilized. Samples are collected at the receptacle housing 38 and can be analyzed separately. The dynamic response of cell samples in the sample containers 40 to stimuli in the solutions from the solution containers is measured.

The solution containers can be of any suitable construction, and can be provided separately or connected to the perifusion device 30. Source containers 50 can be supported on a rack 54 or other suitable supports. Solution can be routed from the source containers 50 through suitable conduits such as flexible tubing. Other source containers or solution sources are possible.

Figure 6:
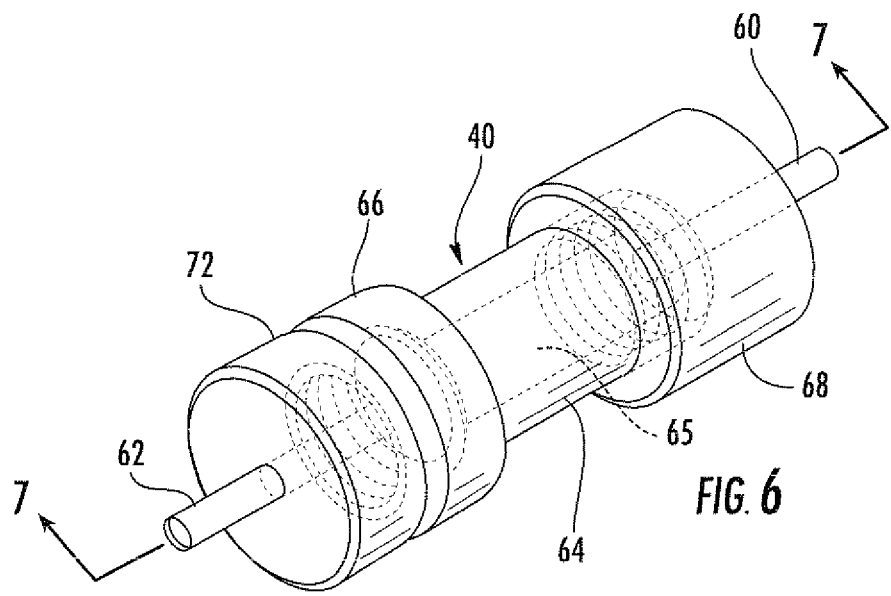
FIG. 6 is perspective view, partially in phantom, of a sample container.
Figure 7:
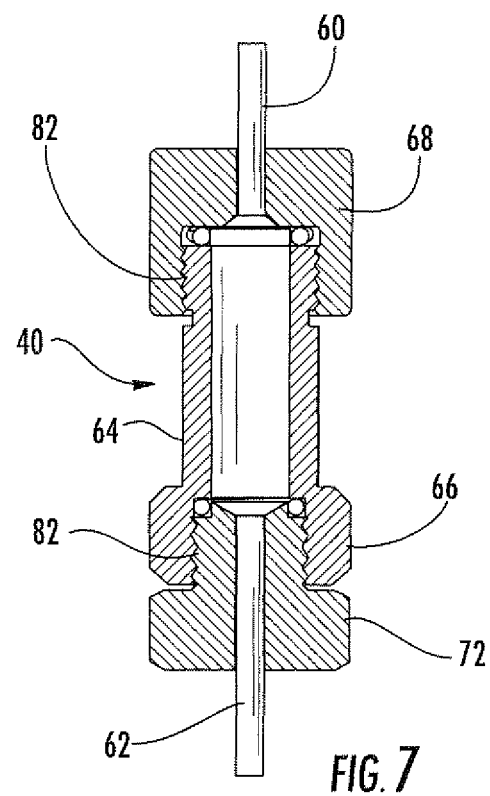
FIG. 7 is a cross section taken along lines 7-7 in FIG. 6.
Figure 8:
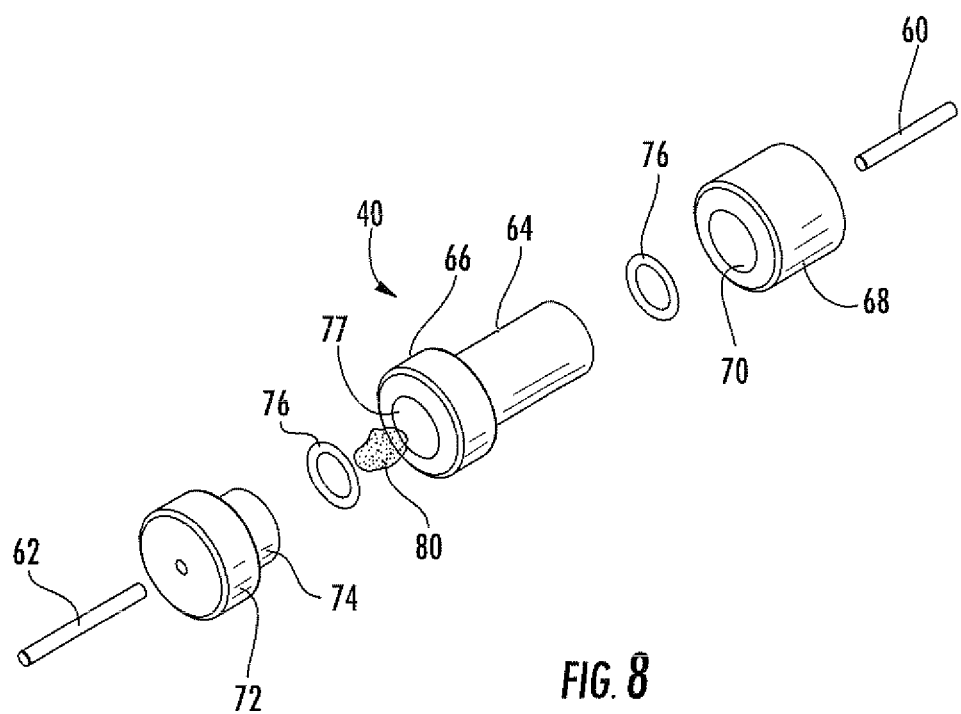
FIG. 8 is an exploded perspective view of a sample container.

A sample container 40 is illustrated in FIGS. 6-8. The sample container 40 can be of any suitable size or construction. In general, the sample container 40 will have an open interior for placement of the sample and will have an inlet 60 and an outlet 62, whereby test fluids can flow into the sample container 40 through the inlet 60, contact the sample, and exit from the sample container 40 through the outlet 62. The sample container 40 can include a main body portion 64 which has an open interior 65. A collar 66 can be provided and has a diameter that is greater than that of the main body portion 64. End cap 68 has an opening 70 adapted to receive an end of the main body portion 64. Inlet 60 is positioned through a suitable opening in the end cap 68. A second end cap 72 has a neck 74 adapted to fit within an opening 77 in collar 66 of main body portion 64. Outlet 62 is positioned within a suitable opening within the second end cap 72. Suitable sealing structures such as o-rings 76 can be provided. The sample 80 is positioned within the open interior 65 of the main body portion 64 and end caps 68 and 72 are secured. Cooperating threads 82 can be used to secure the caps 68, 72 to the main body portion 64.

The valves 40 can be of any suitable construction. In one aspect, the valves 40 are pinch valves which perform the valve function by selectively applying pressure to flexible conduits so as to close the conduit to fluid flow, and then releasing that pressure to permit flow. Other valve and conduit constructions and arrangements are possible.

Figure 10:
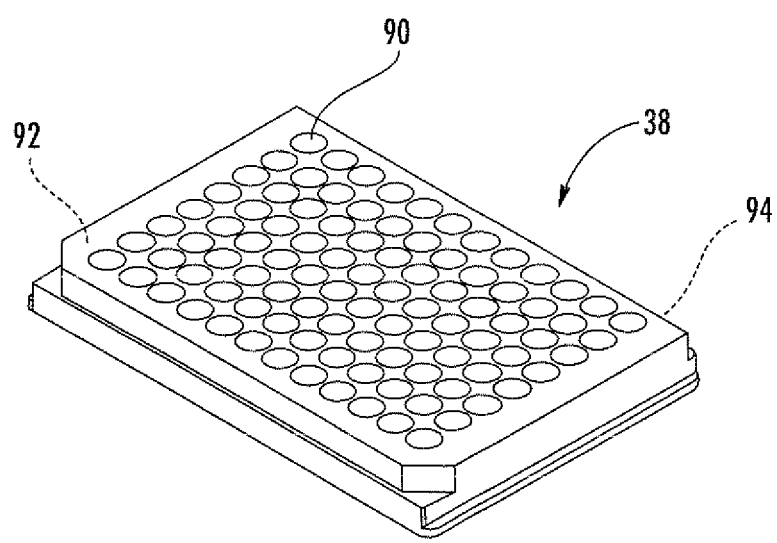
FIG. 10 is a perspective view of a receptacle housing.
Figure 11:
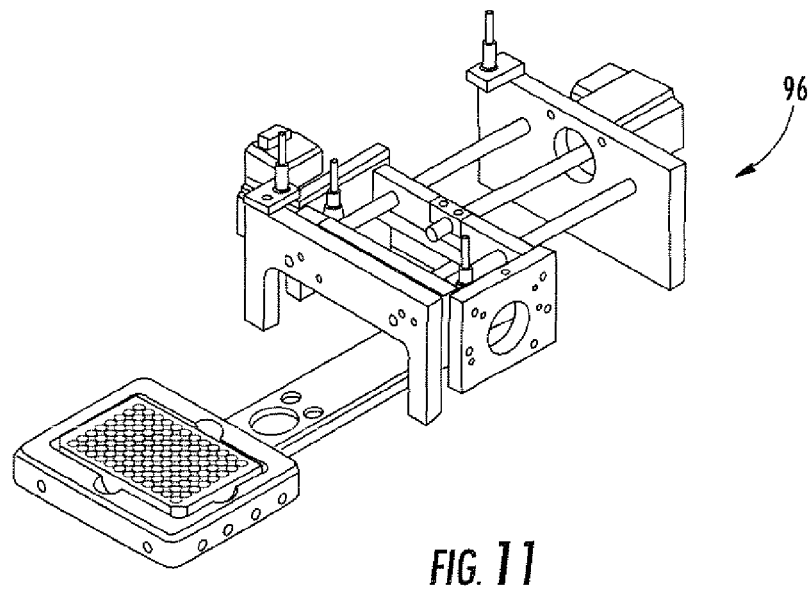
FIG. 11 is a perspective view of a receptacle drive assembly.
Figure 12:
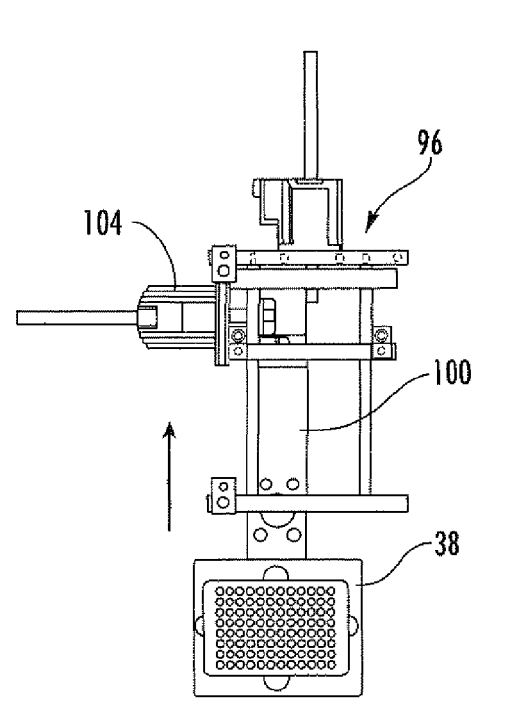
FIG. 12 is a top plan view in a first mode of operation.
Figure 13:
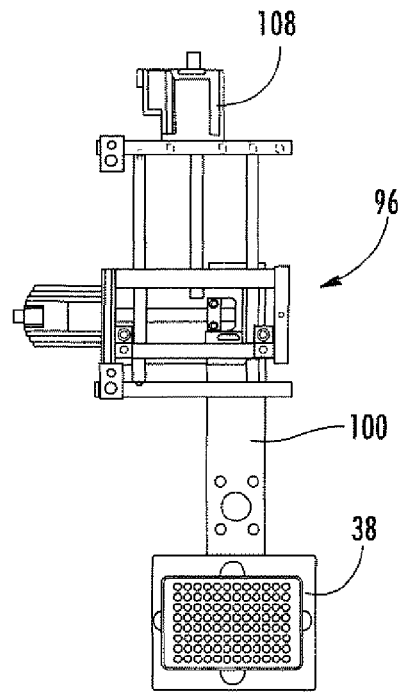
FIG. 13 is a top plan view in a second mode of operation.
Figure 14:
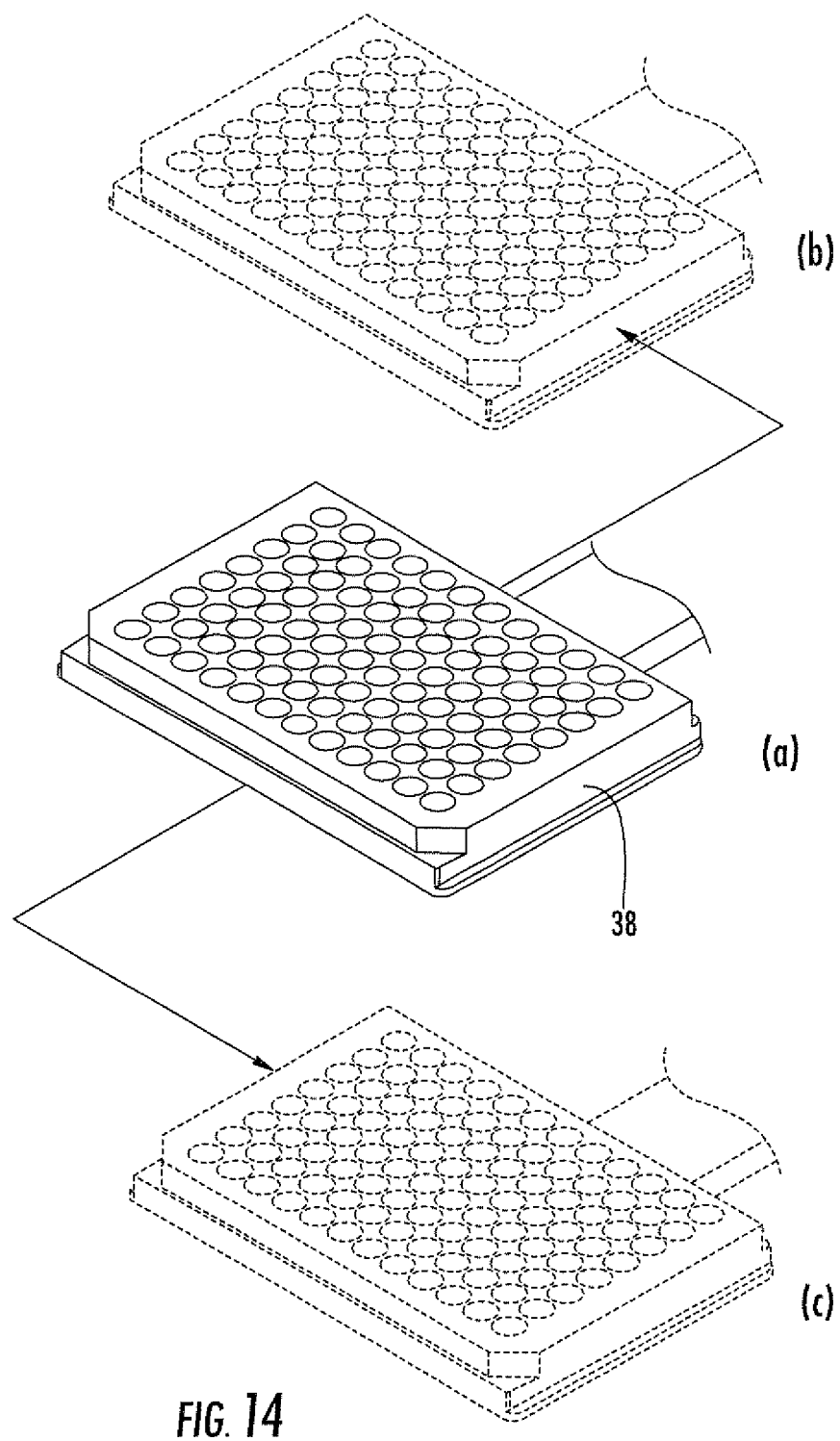
FIG. 14(a-c) is a perspective view, partially in phantom, of a receptacle housing in various modes of operation.

The receptacle housing 38 can also be of any suitable shape. As shown in FIG. 10, the receptacle housing can be a tray having a plurality of suitable receptacles such as wells 90 arranged in rows 92 and columns 94. The receptacle housing 38 is mounted to a drive assembly 96 (FIGS. 11-13) which is capable of incrementally moving the receptacle housing such that wells 90 are sequentially moved to a position to receive subsequent samples from a sample container 40. The receptacle housing can be connected to a drive arm 100 which is in turn connected to a suitable drive assembly. In one aspect, the drive assembly can include a motor 104 for moving the arm to and away from the drive assembly, and a motor 108 for moving the receptacle housing 38 transversely (FIGS. 12-13). Motors 104 and 108 can be operated to move the arm 100 both axially and transversely to position the wells 90 to receive samples from the sample containers 40. The manner in which the receptacle housing 38 is moved, whether axially, transversely or both, can be varied so long as data is maintained as to which well 90 received a sample from which sample container 40 at a given time. Thus the receptacle housing 38 can be moved from the position (a) in FIG. 14, both axially and laterally to the position (b). The receptacle housing 38 can alternatively be moved axially outward and transversely in a different direction to the position (c). Structure can be provided to permit the control of temperature in the receptacle housing 38. Such structure can include heating/cooling channels which receive heating/cooling fluid through fluid connection ports 98.

Figure 15:
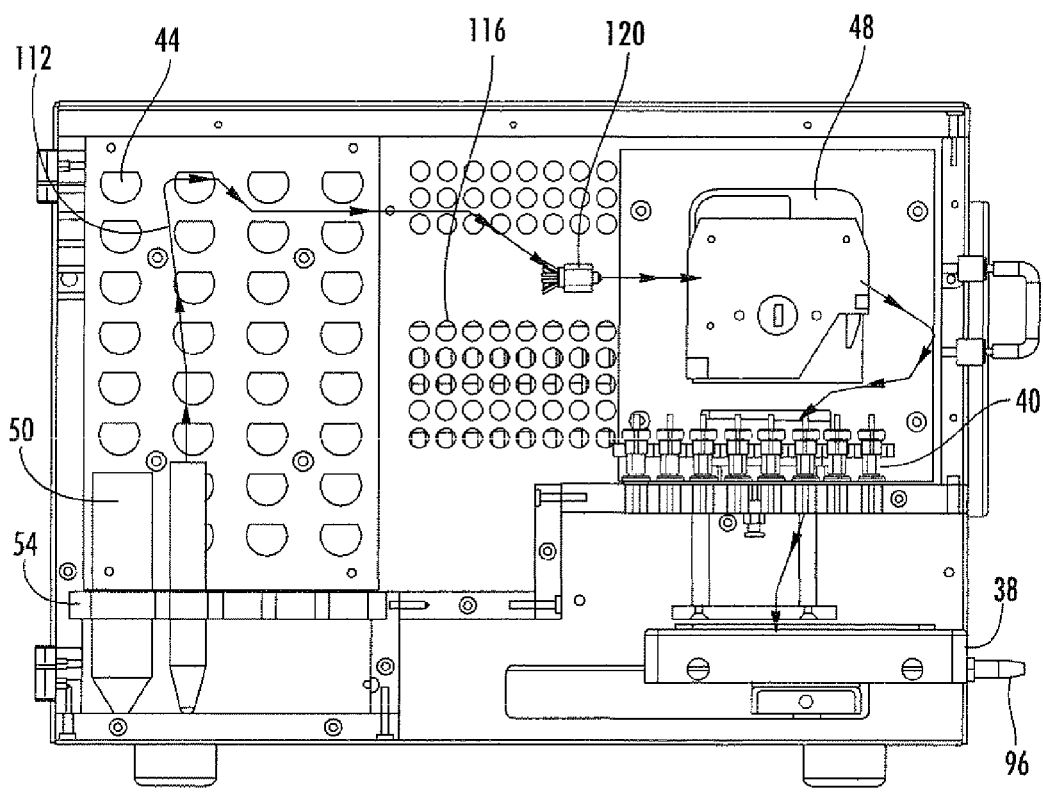
FIG. 15 is a front elevation of a perifusion device illustrating a fluid flow path through the device.
Figure 16:
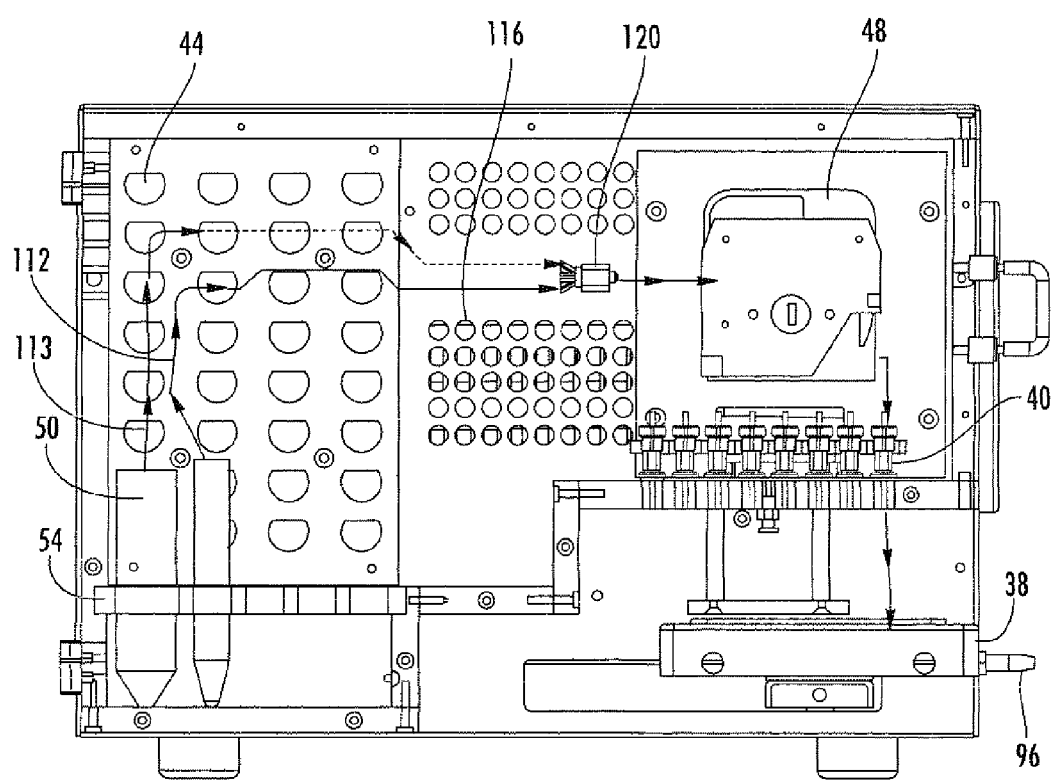
FIG. 16 is a front elevation of a perifusion device illustrating alternative fluid flow paths through the device.
Figure 17:
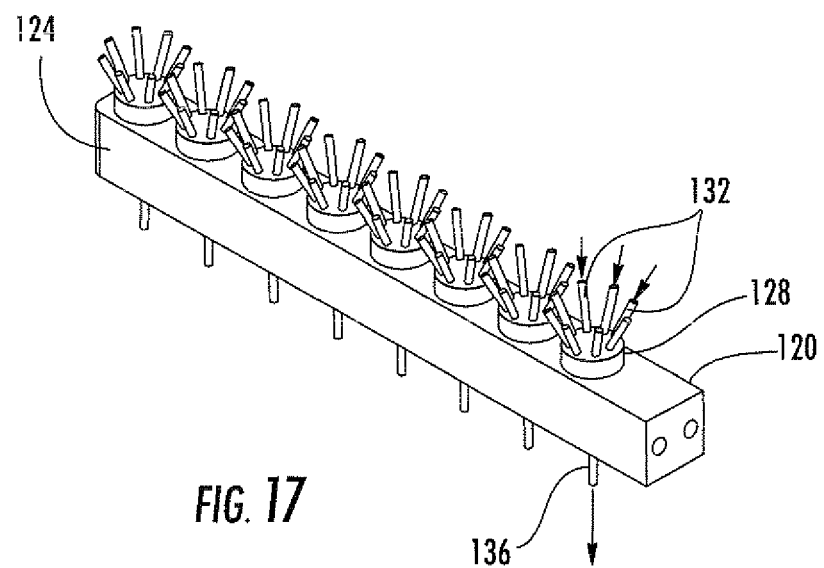
FIG. 17 is a perspective view of a manifold assembly.

Fluid flow through the perifusion device 30 is illustrated in FIGS. 15-16. Fluid from the source containers 50 flows through suitable conduit structure in the direction shown by path 112 past valves 44 to the pump 48. Fluid then flows to the sample containers 40, and through the outlet of the sample container 40 to a well 90 in a receptacle housing 38. Temperature control of fluid in the conduit can be provided by any suitable structure, such as vented heating/cooling air which flows through outlet ports 116 to contact the conduit. Operation of valves 44 can prevent test solution from flowing through path 113 to reach the sample container (FIG. 16), and then the valves 44 can be operated to prevent solution from flowing through path 112.

Figure 9:
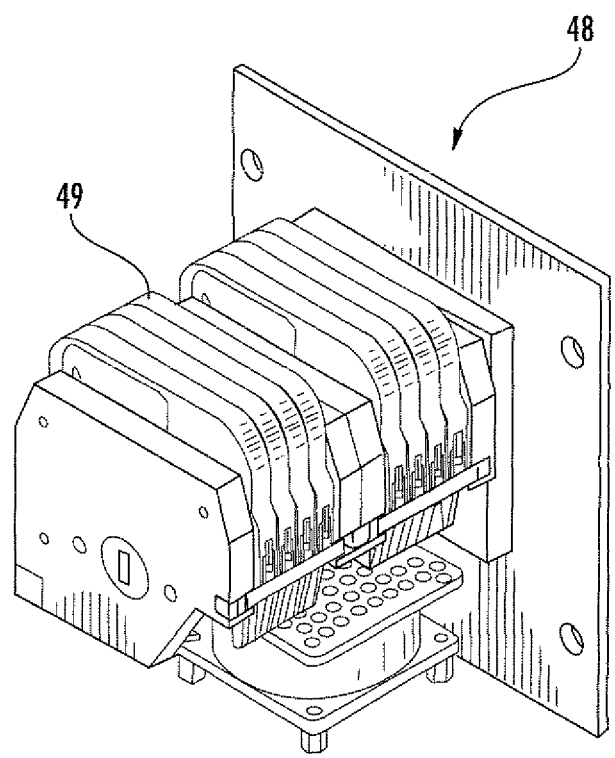
FIG. 9 is a perspective view of a pump assembly.

The pump 48 can be of any suitable construction. In one aspect, the pump 48 is a peristaltic pump having eight channels 49 (FIG. 9). The peristaltic pump preserves sterility by applying pressure through rotating arms to pinch a flexible conduit against a curved surface and thereby move the fluid within the conduit. The pump can have multiple channel 49, whereby a single drive motor can operate separate sets of rollers which operate to pump fluid through separate fluid conduits positioned in the channels. In the illustrated embodiment, the peristaltic pump 48 had eight fluid channel 49, permitting the pumping of fluid through eight distinct conduits. However, more of fewer channels are possible. Also, pumping devices other than peristaltic pumps is possible.

It is possible to have any number of sample containers 40. In the illustrated embodiment, eight sample containers 40 are provided. Different source containers 50 will typically have different solutions for testing samples within the sample containers 40. Also, different testing protocols may be desired for different samples within the sample containers 40. Accordingly, it is desirable to provide flow paths such that solution from one source container 50 can be routed to more than one sample container 40, either simultaneously or sequentially. In the illustrated embodiment, a manifold assembly 120 is provided (FIG. 16). The manifold assembly 120 has support structure 124 and a plurality of individual manifolds 128. Each manifold 128 has a plurality of inlet ports 132, connecting to a single outlet port 136. Any number of inlet ports 132 are possible. In the illustrated embodiment, there are eight inlet ports 132. Operation of the valves 44 permits fluid to flow through one of the ports 132 and the outlet port 136 so as to permit fluid flow therebetween. The remaining inlet ports 132 are closed by operation of valves 44 on the respective conduits connecting to the other ports 132 such that fluid flow through these inlet ports is prevented. It will be appreciated that by use of multiple flow paths from each source container 50, where each flow path is separately controlled by a valve 44, and connects to a manifold 128, that fluid flow from various ones of the source containers 50 to various ones of the sample containers 40 is possible. This permits the control of experiments, whereby differing solutions can be flowed through differing sample containers 40 at different times according to the experimental design.

Computer control can be provided to operate the perifusion device 30. This control can be utilized to operate, among other things, the valves 44, pump 48, and position of the receptacle housing 38 through control of the motors 104, 108. Also, the computer can have internal data storage or can connect to such data storage in order to record the position of the receptacle housing with time such that a record is kept as to the particular samples which were collected in particular receptacles 90 of the receptacle housing 38. Computer control can also control flow rates and temperature, as well as switching of solutions with time according to the experimental design.

Samples are placed within the sample containers 40. The cells will sometimes agglomerate within the sample container 40 during the experiment. The cells can be immobilized within the sample containers 40 by suitable means such as support beads, a gel immobilizer, or other cell immobilizing methods. The beads or gel will separate and support the cells within the container. Solutions are provided in source containers 50 and tubing is connected between the source containers 50, the valves 44, and the sample containers 40. Other systems for providing solutions to the sample containers 40 are possible. The pump 48 is operated to cause the solutions to flow through the sample containers 40. The pump 48 can be manipulated to control the volume flow rate through the sample containers, and can be used to vary this rate if desired for purposes of changing the behavior of the cells. The flow of the solution stimulates the cells to change their behavior.

The test solution can be any solution which will stimulate a change in cell behavior. The stimulus can be the presence, absence or concentration of one or more compounds in the test liquid, or a property of the liquid. The compound can be a carbohydrate, lipid or peptide. The compound can be in the nature of a drug, which stimulates cell behavior in some detectable way. In the case of pancreatic islet cells, the solution can be a glucose solution, or a series of glucose solutions having differing concentrations, or other known insulin stimulants such as GLP-1 or KCl. In other cases, the solution can contain various drugs or substances which effect some change in cell behavior, such as compounds which block cellular receptors. The sample fluid could alternatively contain some substance which is removed by the cells, whereby the extent of removal can provide information about the cells. The stimulus can also be some physical property of the solution, such as temperature or pH.

The system is dynamic as the solutions can be changed with time, such as by changing the concentration of a stimulant or changing the stimulant itself, by switching between source containers 50. Such dynamic characteristics can be used in the case of islet cells to simulate a meal, for example. The receptacle housing 38 is moved to collect samples in wells 90. It is alternatively possible to move the sample containers 40 rather than the receptacle housing 38, so long as they move relative to one another, but movement of the sample containers could change the dynamics of the system by altering cell state within the sample container. Movement of the receptacle housing 38 is controlled such that samples taken from the sample containers can be identified. The samples are then analyzed to detect the change in behavior of the cells. A robot can be used to automatically remove the receptacle housing 38 in order to improve the throughput of the device.

Figure 18:
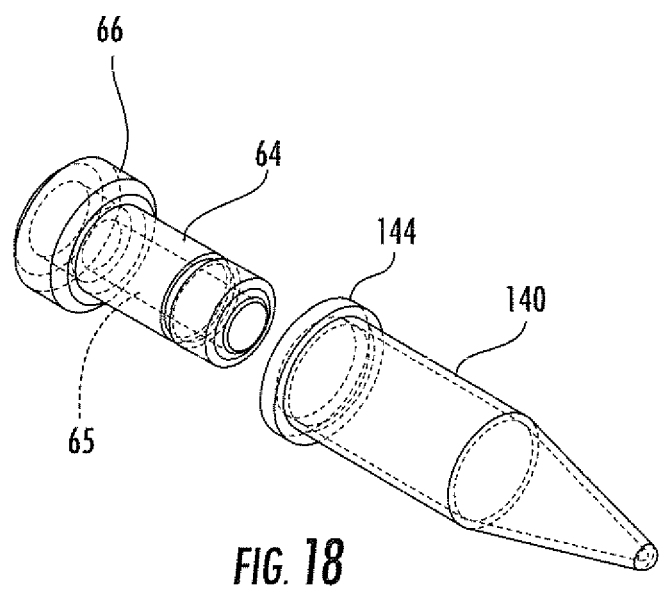
FIG. 18 is an exploded perspective view, partially in phantom, of a portion of a sample container and a microcentrifuge tube.
Figure 19:
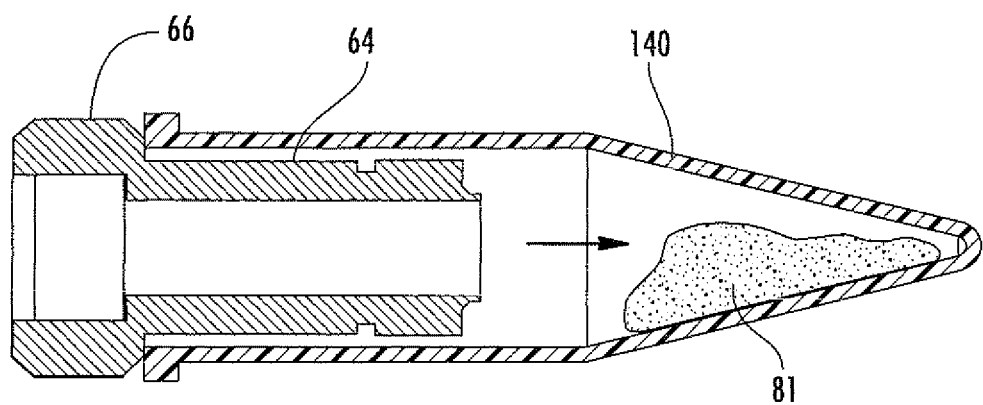
FIG. 19 is a cross section illustrating a portion of a sample container and a sample in a microcentrifuge tube.

Following an experiment, the fluid collected in the wells 90 is analyzed. The method of analysis will depend on the experiment and the characteristics of the fluid sample that are to be determined. Suitable analysis methods can include high speed liquid chromatography, mass spectrometry, and the like. It is also possible to provide one or more sensors in the fluid flow path to analyze such characteristics as oxygen content, pH, turbidity, and others. Such sensors can be provided upstream and downstream from the cell samples so as to detect changes in these characteristics and thereby cell behavior. The cells within the sample containers 40 can also be removed and analyzed. Removal can be accomplished by disconnecting the end cap 68 and 72. The main body portion 64 with the sample within the open interior 65 is then removed. The main body portion 64 is dimensioned to fit within a micro centrifuge tube 140 with the collar 66 seated against lip 144 of the micro centrifuge tube (FIGS. 18-19). In this manner, the sample 81 can be rapidly removed and centrifuged for analysis of the sample 81. The analysis of the cells can be by known techniques. The number of cells in the sample can also be determined to normalize the results of testing for differing numbers of cells in the samples. The number of cells can be ascertained by any suitable method, such as from the amount of DNA in the sample.

Figure 20:
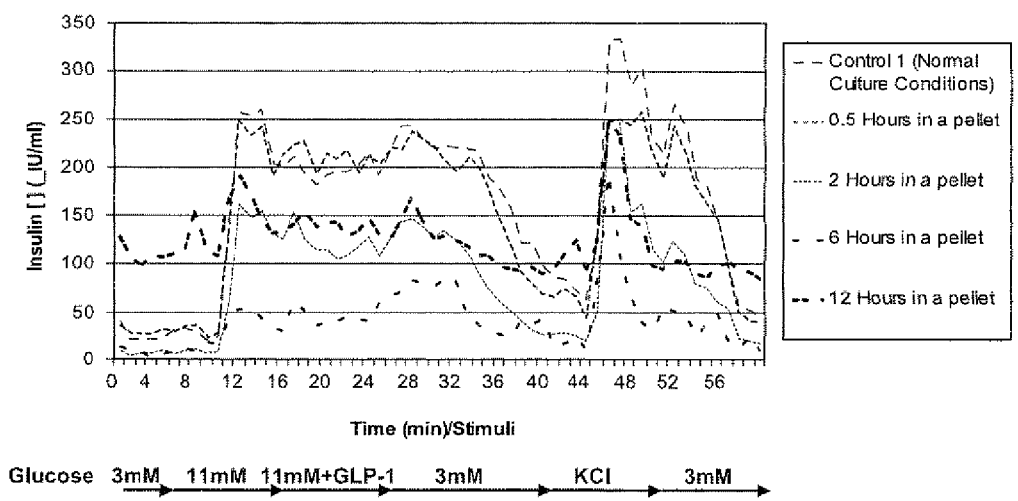
FIG. 20 is a graph of insulin release versus time from stimuli after anoxic conditions.
Figure 21:
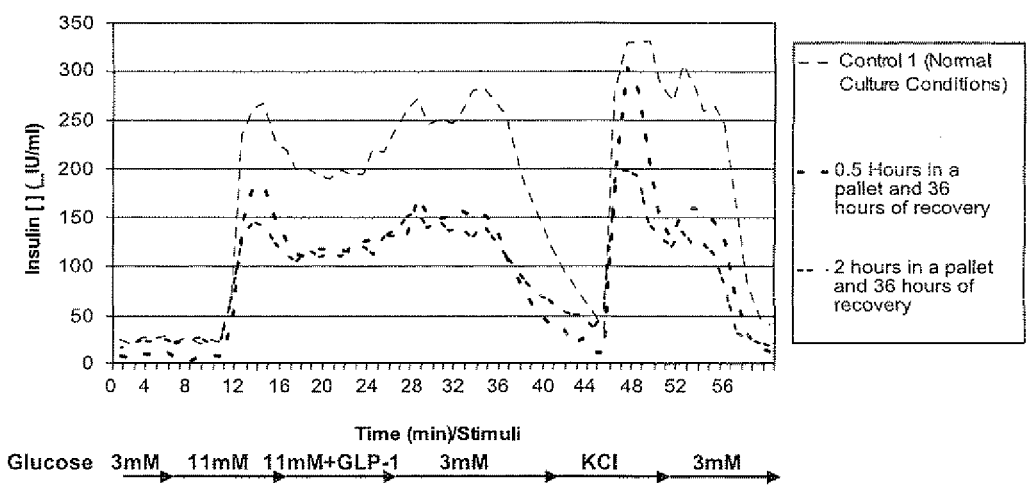
FIG. 21 is a graph of insulin release versus time from stimuli after anoxic conditions and 36 hours recovery time.
Figure 22:
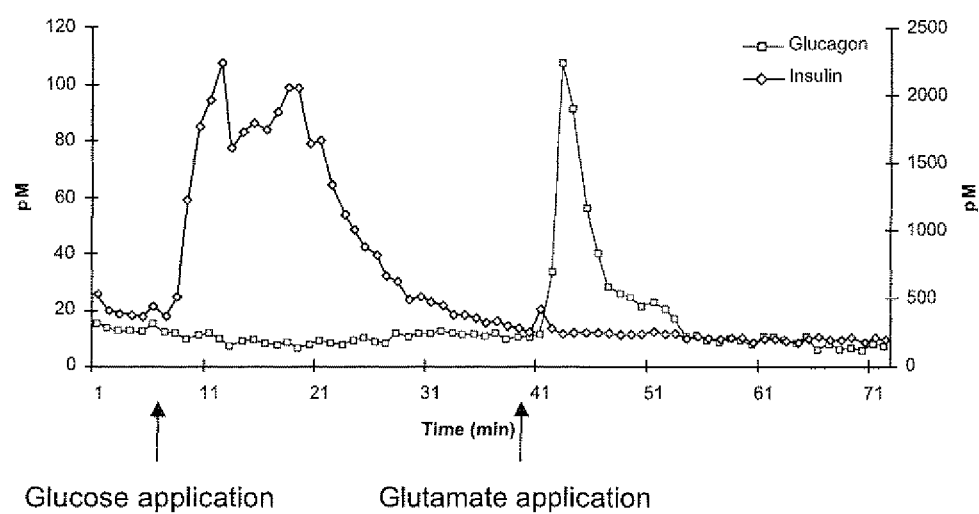
FIG. 22 is a graph of glucagon/insulin release versus time.

FIGS. 20-22 illustrate experimental results using the perifusion device 30 according to the invention. FIG. 20 illustrates insulin release by perifusion with time. Islet cells were compromised by depriving them from the normal oxygen concentration for 0.5, 2, 6, and 12 hours. After that, these islets were incubated in the perifusion system and exposed to substances that stimulate insulin release such as 11 mM of glucose, GLP-1 in addition to 11 mM of glucose, and potassium chloride (KCl). The profile of insulin release measured by ELISA of the samples collected from the perifusion system indicates that islets responded to the stimuli in a way that is proportional to the health of the islets. The control batch, normal culture conditions without oxygen deprivation, showed a prominent response to all three stimuli. Two and six hours of oxygen deprivation diminished the response in agreement with the time these cells were incubated with low oxygen. In the case of twelve hours of incubation with low oxygen, the health of the islets seem to be irreversibly compromised. The cells had little or no response to 11 mM glucose and GLP-1, and the KCl response was very small. These cells are constantly secreting insulin in a non-regulated fashion, as shown by the passive release at 3 mM glucose. This may indicate that this batch of islets is severely damaged.

FIG. 21 illustrates insulin released by perifute in which pancreatic cells were deprived from oxygen but their ability to secrete insulin in response to stimuli was not tested until thirty-six hours after they had been removed from the anoxic conditions (recovery time). Again, an insulin release assay using the perifusion system is indicative of the health of the islets. Even though these islets were allowed to recover from the anoxic trauma, their insulin release profile indicates that their potency had been diminished by the adverse conditions to which they were exposed (low oxygen). Therefore, the perifusion assay not only can provide information about the current status of the islets, but also can give clues about past traumatic conditions and how much these conditions affected the islets. Six and twelve hours of oxygen deprivation was so traumatic to the islets that the majority of these cells died and could not be assayed after thirty-six hours.

FIG. 22 illustrates glucagon-insulin release from in vitro perifused human islets. This experiment was conducted to show the usefulness of the perifusion system in drug screening. Insulin and glucagon are hormones secreted from the beta and alpha cells of the islets of Langerhans. The release profile was measured in the perifusion system after stimulation with glucose which stimulated the beta cells to release insulin and kainates which stimulated the alpha cells to produce glucagon. The figure demonstrates a very prominent and clean release profile for each compound. In the same way, any other compound's ability to influence the health or alter the behavior of the pancreatic islets can be assayed using the perifusion system of the invention.

There is shown in FIGS. 23-31 a perifusion device 200 according to alternative embodiments of the invention. A plurality of source containers 208 are used to store liquids that will be used in the testing of samples. A valve manifold assembly 212 receives liquid from the source containers 208 through liquid conduits (not shown) connecting the source containers 208 to the valve manifold 212 having a plurality of valves 214. A pump assembly 216 moves liquid from the source containers 208 and the valve manifold 212 to sample containers 220. Samples exit the sample containers 220 and are collected in a receptacle housing 224. The receptacle housing 224 can rest on a receptacle support 228 that is movable by drive arm 232. The receptacle support 228 can have interior cooling channels for cooling water or gas, which receive and exhaust the cooling fluid through fittings 230.

Figure 23:
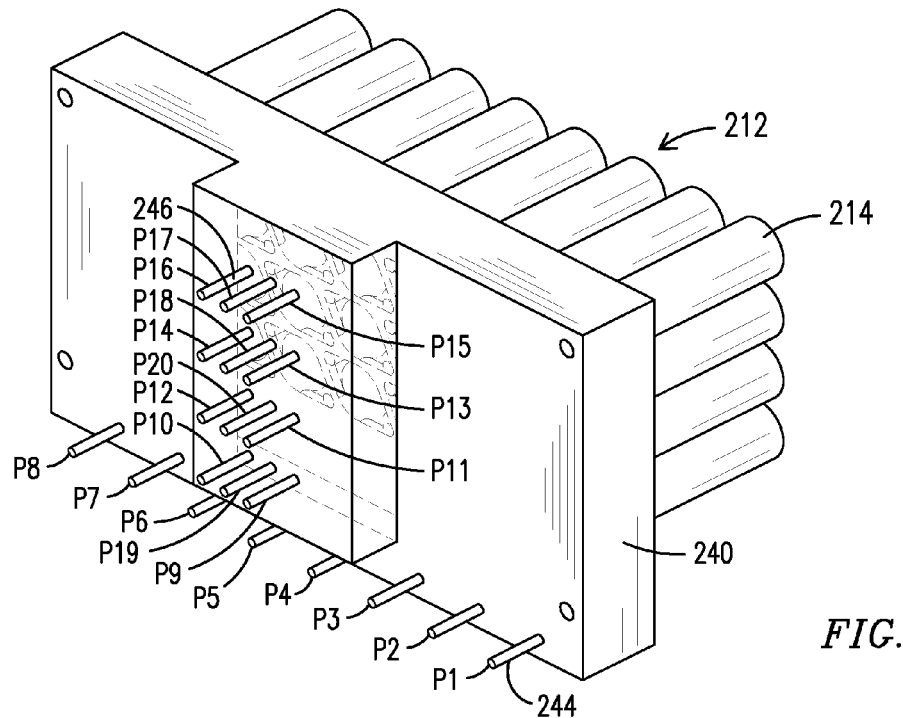
FIG. 23 is a perspective view of a valve manifold assembly according to an alternative embodiment of the invention.
Figure 24:
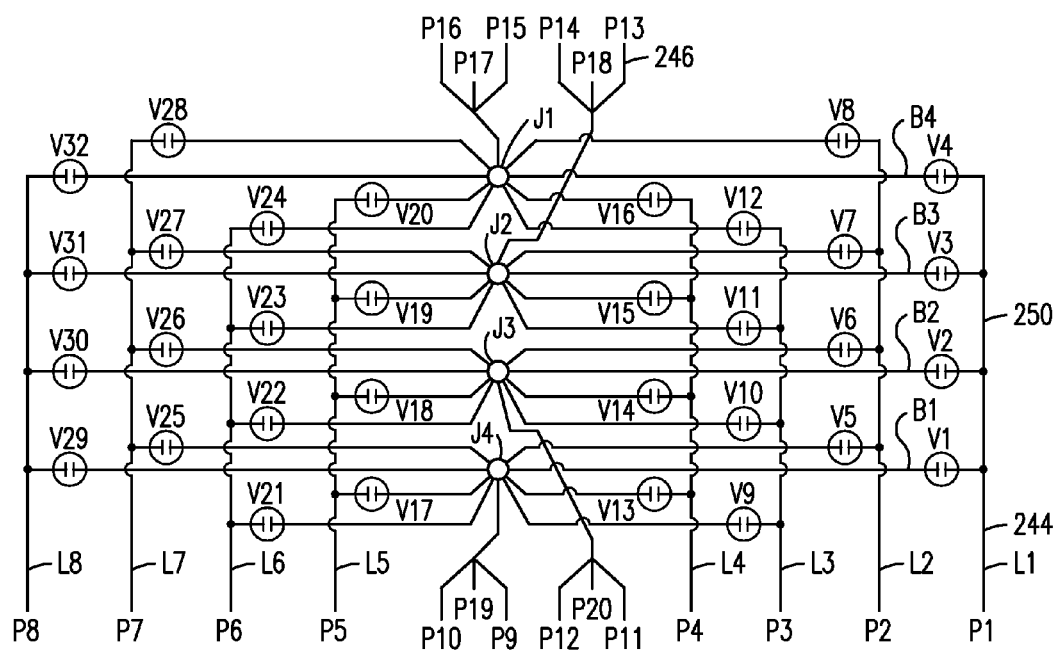
FIG. 24 is a schematic representation of liquid flow paths through the manifold of FIG. 23.
Figure 25:
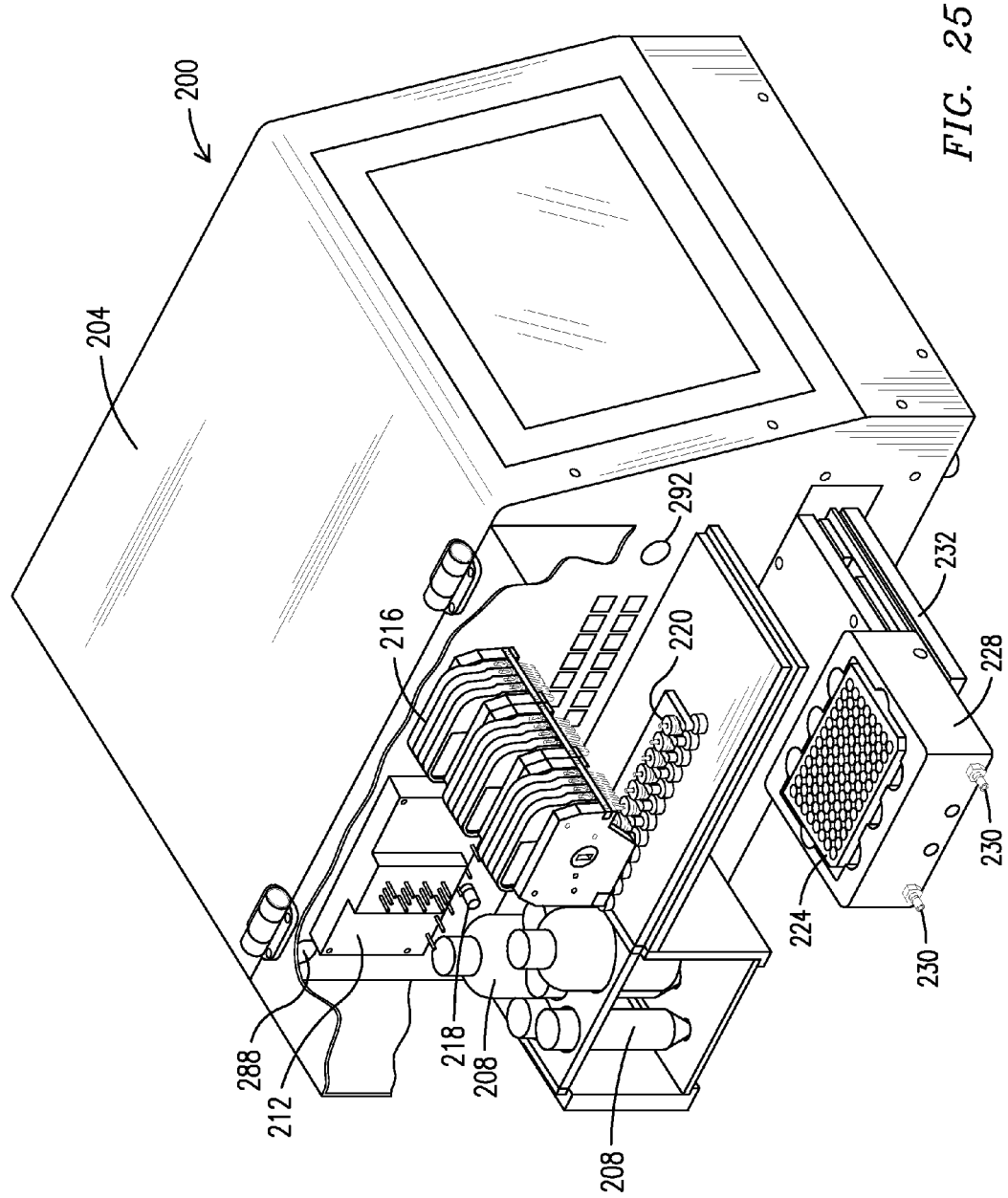
FIG. 25 is a perspective view of a perifusion device according to an alternative embodiment.
Figure 26:
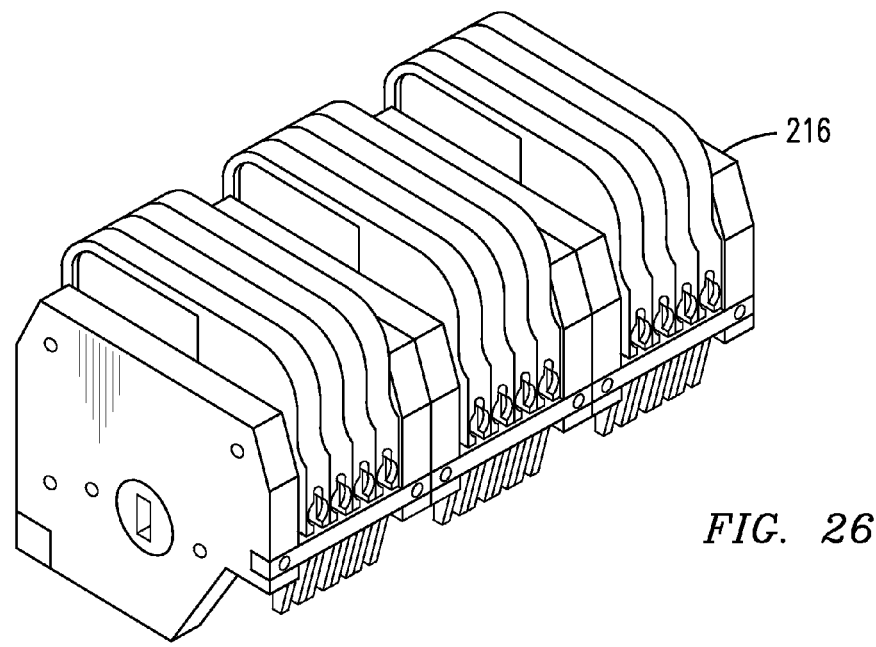
FIG. 26 is a perspective view of a pump head assembly according to the alternative embodiment.
Figure 31:
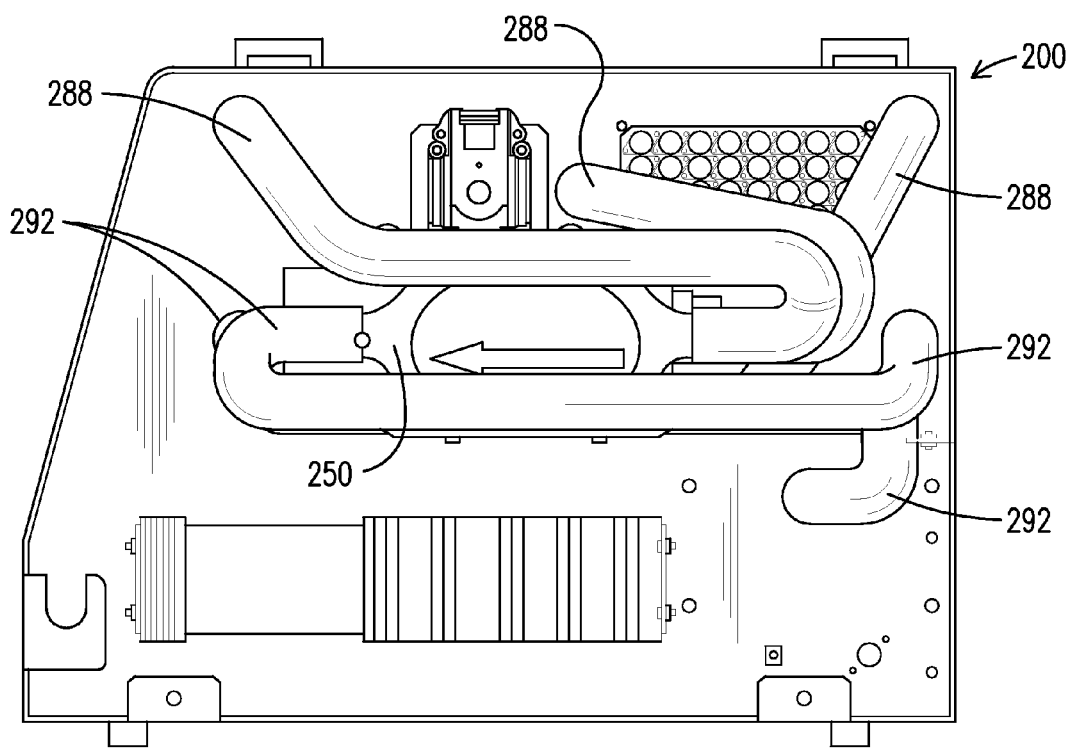
FIG. 31 is a rear elevation of a perifusion device according to an alternative embodiment.

The valve manifold 212 has a manifold housing 240 (FIG. 23). A plurality of liquid inlets 244 and liquid outlets 246 is provided. Within the manifold housing 240 is a plurality of liquid channels. Any number of liquid channels can be provided. An example of one possible arrangement of liquid channels 250 within the housing 240 is shown in FIG. 24. The liquid inlets 244 are identified as P1-P8. The liquid outlets 246 are identified as P9-P20. Liquid flows from the inlets P1-8 through a series of inlet lines L1-L8. Branches from the lines L1-8 lead to valves V1-V32, and to flow junctions J144, and from there to outlets P9-20. Identification of each inlet, valve, flow junction, and outlet allows for computer control of mixing and throughput in a desired fashion. The liquid inlets 244, outlets 246, flow junctions J1-4, and valves 214 can all be connected to or contained within the manifold housing 240. Different numbers and arrangements of inlets, outlets, valves and flow junctions are possible. In some instances it is desirable to deliver a gas to the solutions prior to entry into the sample containers 220. Examples of gases delivered in during cell incubation and diagnostic procedures can include, without limitation, oxygen and nitrogen. A fitting 218 can be provided for this purpose. The fitting 218 can either deliver gas directly to the source containers 208 or supply lines through injection fittings, or alternatively can supply gas to the incubator in general and the tubing can be selected so that the gas diffuses through the tubing into the solution.

Flow through the manifold can be illustrated with reference to a single liquid inlet, P1. Liquid entering the valve manifold 212 through the inlet P1 flows through liquid channel L1 and can branch through one of four branch lines B1-B4 leading to flow junctions J1-4. Valves V1-4 are positioned to control flow from P1 through the branch lines B1-4 to the respective flow junctions J1-4, so that different liquid mixtures can be made by selectively controlling the valves. Similarly each of the inlets P1-8 can have branch lines leading to flow junctions J1-4 and flow to the flow junctions can be controlled by valves V1-32. In this manner, flows from various liquid sources can be selectively controlled so that mixtures of different liquids and different liquid concentrations are possible if the materials and concentrations in the respective source containers 208 is known by the computer that is controlling the pumps and valves. The liquid mixtures exit through the liquid outlets P9-20 to sample containers 220 where the samples are contacted with the liquids.

The valve manifold 212 can be manufactured by many suitable methods. In one method, the valve manifold 212 is manufactured using 3D printing technology such as stereolithography (SLA) by printing with a suitable material such as Watershed 11122 by DSM N.V. of Heerlen, Netherlands. It also is possible to machine layers or halves of the manifold, such as from acrylic or polyetherimide, and then bond them together.

The valves 214 can be any suitable valves. In one aspect the valves are solenoid operated diaphragm valves, such as the Lee MW flange mount valve (The Lee Co., Essex, Conn.). The operating parameters of the valves will depend on many factors such as the flow rates, viscosity, and make-up of the materials flowing through the valves.

The pump 216 can be any suitable pump. In one embodiment shown in FIG. 26, the pump head is a 12-channel peristaltic pump, such as the ISM737A pump manufactured by ISMATEC SA of Glattbrugg, Switzerland. The pump head is operated by a suitable motor. It will be appreciated that the number of pump channels that are necessary will in party depend on the number of source containers 208, sample containers 220, and the number of liquid lines flowing from and into those containers.

Figure 27:
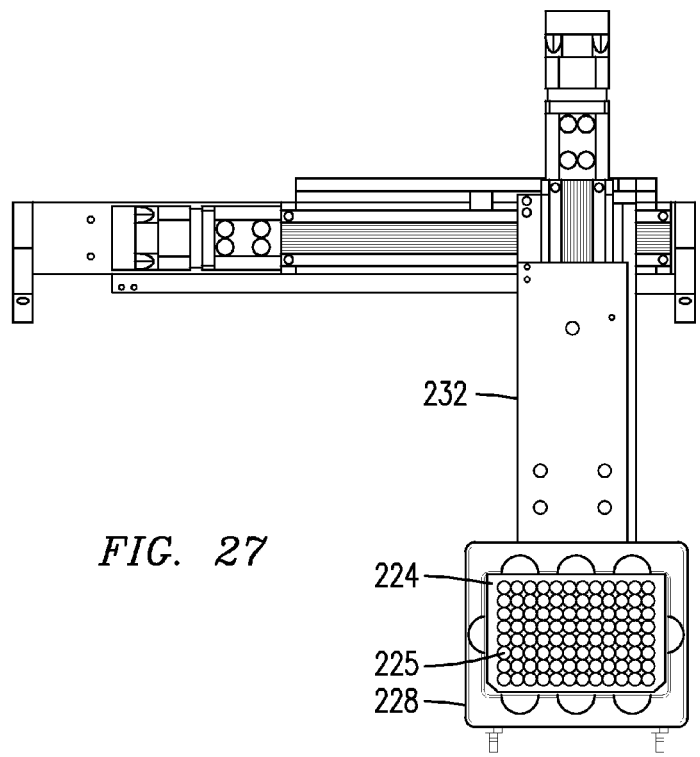
FIG. 27 is a top plan view of a receptacle drive assembly according to an alternative embodiment of the invention, in a first mode of operation.
Figure 28:
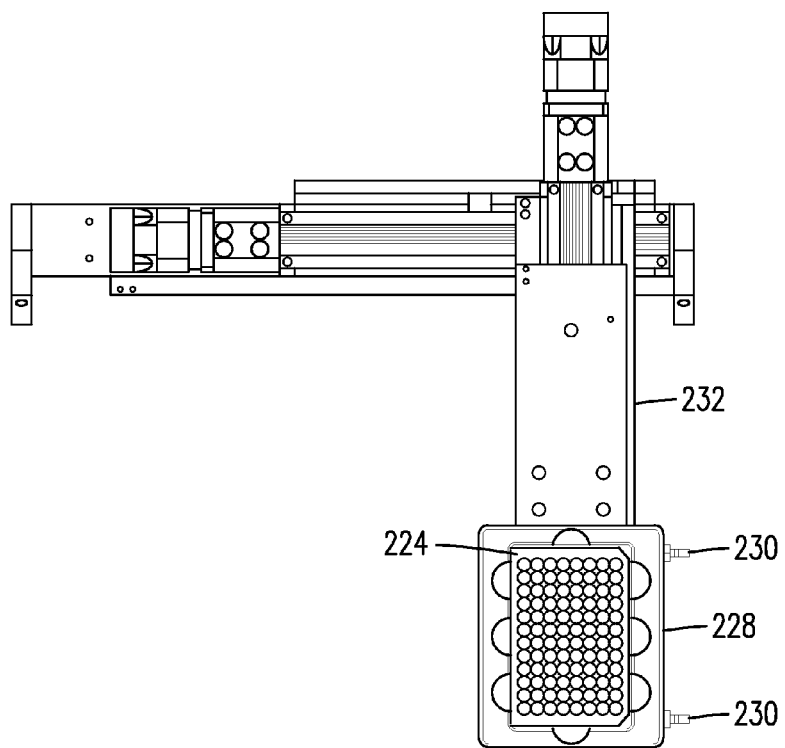
FIG. 28 is a top plan view of a receptacle drive assembly according to an alternative embodiment of the invention, in a second mode of operation.

The receptacle housing 224 can be a tray having a plurality of wells 225. Any number of wells 225 is possible (FIGS. 27-28). The wells can be dimensioned to receive the appropriate amount of material for the test, and deep wells are possible where significant amounts of material must be collected. The receptacle housing 224 can be positioned on the receptacle support 228 in both landscape (FIG. 27) and portrait (FIG. 28) configurations. The receptacle support 228 is driven by the drive arm 232, the movement of which is controlled by a suitable computer or other controller to move the receptacle housing 224 according to the desired.

The outlets of the sample containers 220 are preferably dimensioned to result in small droplets into the wells 225. Smaller droplets permit better control of droplet flow into the wells 225 and better resolution of the data. Larger droplets, such as the approximately 30 µL droplets that typically emanate from laboratory silicone tubing, can effect data results depending on which well 225 a droplet falls into as the receptacle housing 224 moves. A preferable droplet size is 0.1-10 µL, or 1-5 µL, 0.5-2 µL, or 5-7 µL. Stainless steel nozzles have an outlet opening of between about 0.001" to 0.010" ID are preferable. To minimize drop size, the inner bore of the outlet should be as smooth as possible, made from or covered by a low friction material such as PTFE, and the tip should be cut at an angle such as 45 deg. so that the surface area from which the drop can hang is minimized.

A heater assembly 250 is provided to heat and circulate heated air so as to maintain the temperature of the liquids at or near a desired temperature. The heater assembly can include a housing 254 with air intakes 258 and air outlets 262. A heating element 272 and heat dissipator 274 can be provided to heat the air flowing through the heating assembly 250, and can receive power through electrical contacts 280. The heat dissipator 274 is an aluminum or other heat-conductive piece which is heated by the elements 272 by conduction. The dissipator 274 has many holes to permit the passage of air, and as the air flows through the heated dissipator 274 the air will also heat, and the heated air then flows through the air outlets 262. A fan or blower 276 is provided to circulate the air. Inlet ducts 288 deliver air to the perifusion device 200 and exhaust ducts 292 remove the air. The heater assembly 250 can be made responsive to temperature sensors which sense the temperature of the liquid and provide this information to the computer or controller to control operation of the heating element 272 and/or the blower 276, and thereby influence the temperature of the liquids.

The computer or controller can be any intelligent device capable of being programmed to operate the valves, pumps, heater and drive arm. This can be a computer or computer application, either onsite or web-based, or any one of many different types of programmable controllers. In one embodiment the controller is the NI cRIO-9073 Integrated 266 MHz Real-Time Controller and 2M Gate FPGA manufactured by National Instruments of Austin Tex. In another embodiment the controller is the CP1H-XA40DT-D manufactured by Omron Electronics LLC of Schaumburg Ill.

Figure 32:
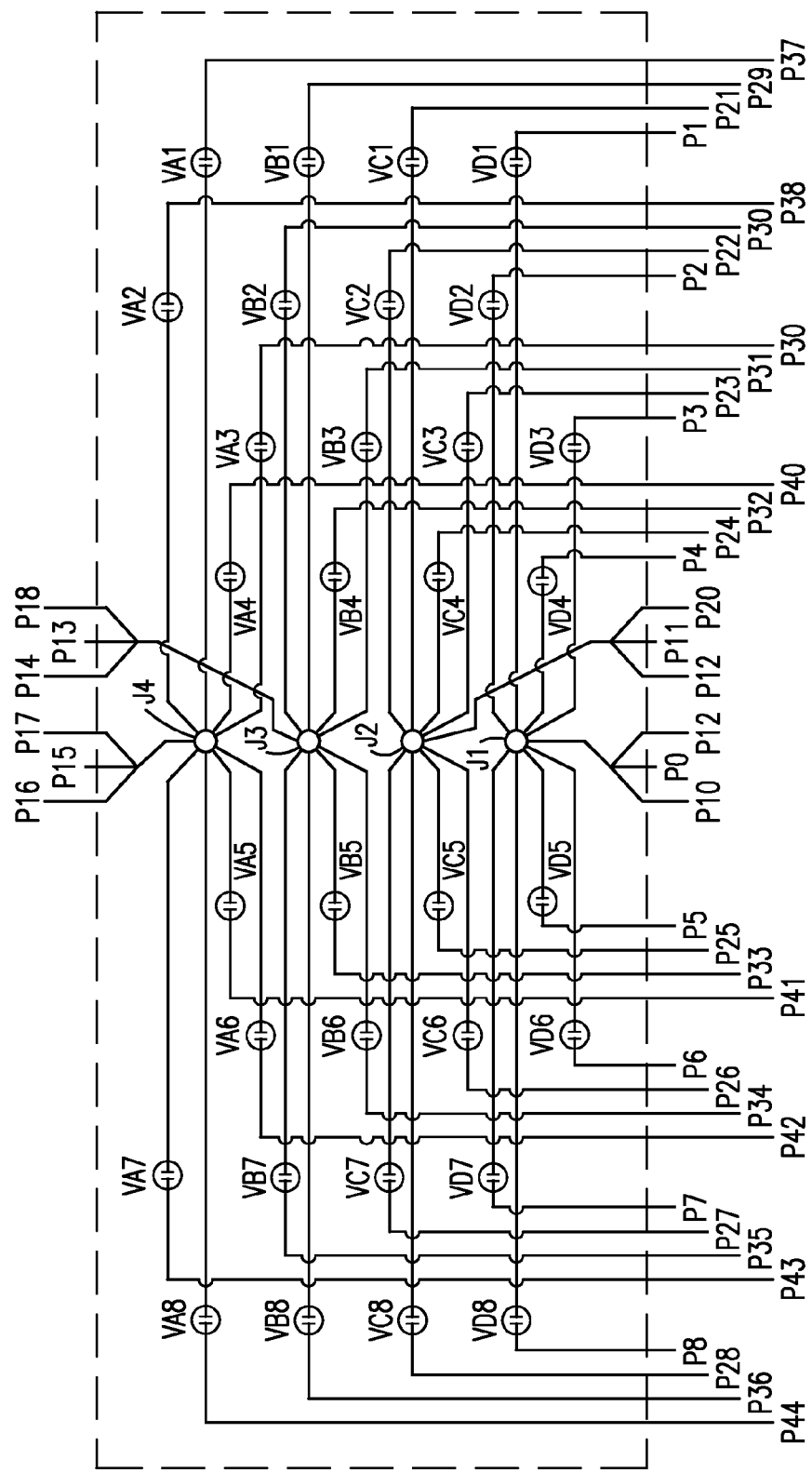
FIG. 32 is a schematic diagram of an alternative valve manifold design.

There is shown in FIG. 32 a schematic diagram of an alternative valve manifold design in which 32 inputs P1-32 are provided with 32 valves VA1-8, VB1-8, VC1-8, and VD1-8, so that flow through each inlet can be individually controlled. Flows are combined in flow junctions J1-4. Liquid leaves the manifold through liquid outlets P9-20.

Figure 33:
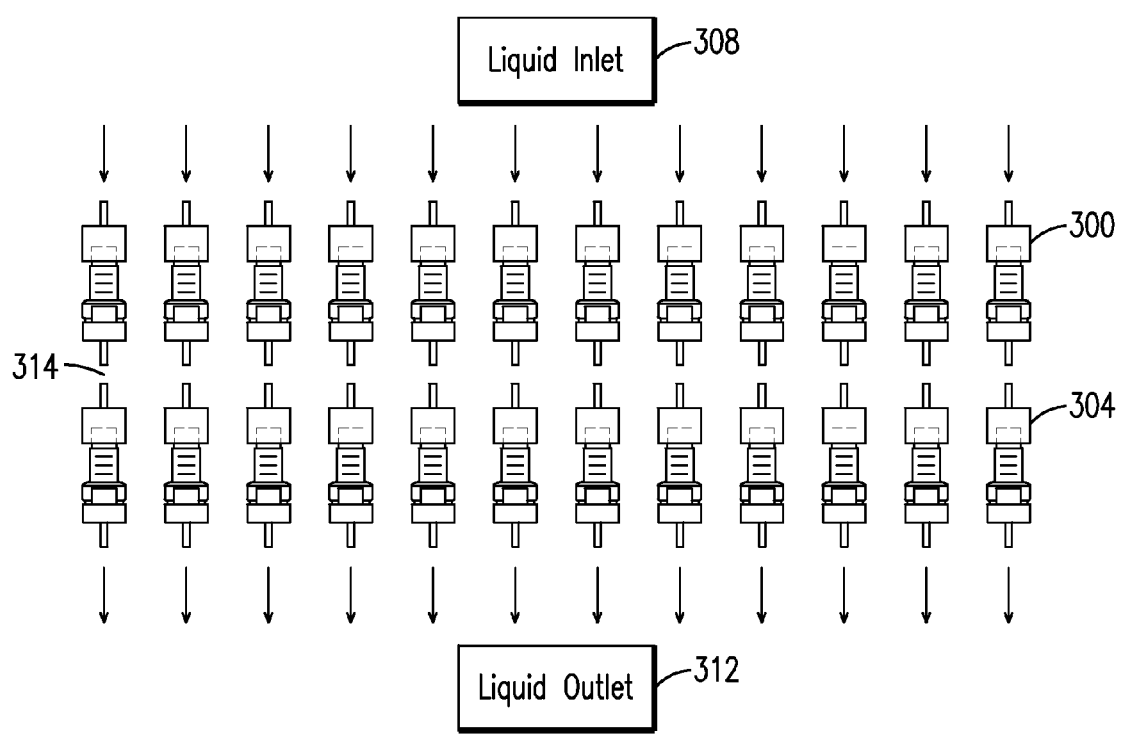
FIG. 33 is a schematic flow diagram of an alternative perifusion system according to the invention.

It is also possible to provide for series orientation of at least some of the sample containers, such that the output of one sample container becomes the input of another sample container. Such a system is shown in FIG. 33, where liquid from an inlet 308 flows first through sample containers 300 and then through sample containers 304 to the output 312. A suitable liquid connection such as tubing 316 can direct liquid from the sample containers 300 to the sample containers 304.

Figure 34:
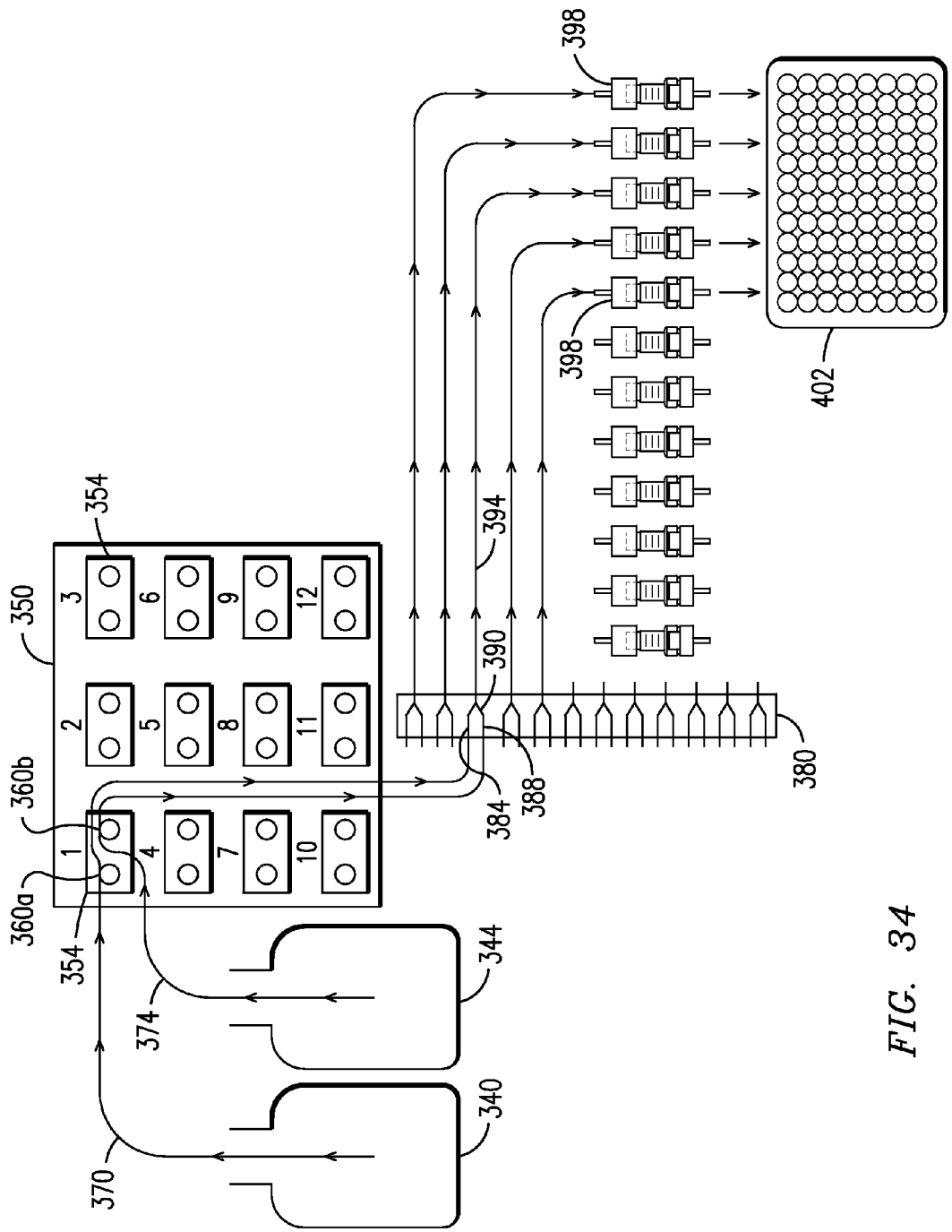
FIG. 34 is a schematic flow diagram of a variable concentration perifusion system according to the invention.

It is possible to control the concentration of materials flowing into the sample containers. One such system is shown in FIG. 34 in which two source containers 340 and 344 are provided with differing concentrations representing the higher and lower concentrations of a substance to be mixed, for example glucose. The desired concentration must be the same or between the two concentrations in source containers 340 and 344. A pump assembly can have a plurality of pump pairs 354, where one pump pair is allocated for each desired output. Pumps 360a,b control flow through lines 370, 374 and are capable of controlling flow rates very carefully. Knowing the concentration in each source container 340 and 344, the flow rates can be calculated and controlled and the flows mixed together to result in a final concentration between the concentrations in the source containers 340 and 344. A manifold 380 can be provided with branch lines 384, 388 leading to flow junction 390 such that the combined flow through output line 394 leading to sample container 398 is of the desired concentration and can then be collected in receptacle housing 402. For example, if source container 340 has a 0% concentration of a desired substance and source container 344 has a 100% concentration, then combining both flows equally will result in an output solution that has a concentration of the substance of 50%.

This invention can be embodied in other forms without departing from the spirit or essential attributes thereof and, accordingly, reference should be had to the following claims rather than the foregoing specification as indicating the scope of the invention.

We claim:

1. A method for performing perifusion, comprising the steps of:

providing a perifusion device, said perifusion device comprising a plurality of sample containers having a liquid inlet and a liquid outlet, the containers receiving liquid through the inlet and discharging through the outlet; a receptacle housing having a plurality of receptacles for receiving liquid from the outlet of the sample container, said plurality of receptacles being positioned in said receptacle housing such that different receptacles receive samples from different liquid outlets of said sample containers; a drive connected to the receptacle housing for moving said receptacle housing such that samples from the liquid outlets of said sample containers are successively collected in different ones of said plurality of receptacles; a valve manifold having a plurality of manifold liquid inlets and a plurality of manifold liquid outlets, and a plurality of flow junctions connecting said manifold liquid inlets to said manifold liquid outlets, and at least one valve disposed between each manifold liquid inlet and each flow junction, wherein each of said liquid inlets is connected to a liquid inlet conduit of said manifold, said liquid inlet conduit having a plurality of branch lines, each branch line being connected to at least one of said flow junctions and having at least one valve associated with said branch line to control liquid flow through said branch line and to said flow junction; a plurality of liquid sources for supplying liquid to said containers, each liquid source being connected to one of said manifold liquid inlets of said valve manifold; said manifold liquid outlets of said valve manifold being connected to said liquid inlets of said sample containers; and, a programmable controller for controlling the operation of said valves and the flow of liquid from said liquid sources to the flow junctions, and thereby to the sample containers;

placing sample cells into said containers;

providing in at least one of said liquid sources at least one stimulus for said cells;

causing said liquid containing said stimulus to flow through said valve manifold;

operating said programmable controller to cause said valves to control the flow of liquids from said liquid sources to said flow junctions, said liquids being mixed in said flow junctions and exiting through said manifold liquid outlets to said inlets of said sample containers;

collecting said liquid from said liquid outlets of said sample containers in said receptacles;

causing said drive to move said receptacle housing;

collecting at least one additional sample in at least one additional receptacle; and, detecting the response of the cells to the stimulus in said collected samples.

2. The method of claim 1, wherein each flow junction connects to a plurality of liquid outlets of said valve manifold.

3. The method of claim 1, wherein each flow junction connects to a plurality of said branch lines and to a plurality of liquid inlets and liquid sources.

4. The method of claim 1, wherein said receptacles are arranged in rows and columns and said liquid outlets of said sample containers are aligned in a row, said rows of receptacles being aligned with said row of liquid outlets to receive samples from said sample containers, movement of said receptacle housing by said drive causing successive rows of receptacles in said columns to receive successive samples from said sample containers.

5. The method of claim 1, wherein said receptacle housing is a tray, said tray being detachably secured to a receptacle drive assembly in either landscape or portrait positions.

6. The method of claim 1, further comprising the step of heating gas flowing through said perifusion device.

7. The method of claim 1, wherein said receptacles are wells.

8. The method of claim 1, wherein said sample containers are columns.

9. The method of claim 8, further comprising the step of pumping said liquid to flow through said column with a pump.

10. The method of claim 9, wherein said pump controls the volumetric flow rate through said container.

11. The method of claim 9, wherein said pump is a peristaltic pump.

12. The method of claim 1, further comprising the step of packing the sample containers with substrate.

13. The method of claim 12, wherein said substrate comprises at least one selected from the group consisting of beads and gel.

14. The method of claim 1, further comprising the step of operating said drive with a programmable controller to move said receptacle housing at predetermined times.

15. The method of claim 14, wherein said programmable controller is a computer.

16. The method of claim 1, further comprising at least one sensor for sensing a characteristic of the liquid.

17. The method of claim 16, further comprising the step of sensing the liquid with at least one sensor upstream of the sample and at least one sensor downstream of the sample.

18. The method of claim 1, wherein said liquid comprises a cell stimulus compound, said compound being at least one selected from the group consisting of carbohydrate, lipid, and peptide.

19. The method of claim 1, wherein said cell stimulus compound comprises a drug which stimulates cell behavior in some detectable way.

20. The method of claim 1, further comprising the step of controlling the temperature of said liquid flowing through said sample container with at least one temperature controller.

21. The method of claim 1, comprising first and second sample containers, the output of said first sample containers flowing into and becoming the input for said second sample containers.

* * * * *